(12) United States Patent
Fukuma et al.

(10) Patent No.: US 7,784,941 B2
(45) Date of Patent: Aug. 31, 2010

(54) FUNDUS OBSERVATION DEVICE

(75) Inventors: Yasufumi Fukuma, Tokyo (JP);
Hiroyuki Otsuka, Tokyo (JP);
Kazuhiko Yumikake, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 11/621,676

(22) Filed: Jan. 10, 2007

(65) Prior Publication Data

US 2007/0159595 A1   Jul. 12, 2007

(30) Foreign Application Priority Data

Jan. 10, 2006  (JP) .............................. 2006-003065
Jan. 10, 2006  (JP) .............................. 2006-003066

(51) Int. Cl.
*A61B 3/10* (2006.01)
(52) U.S. Cl. ..................................... 351/205; 351/221
(58) Field of Classification Search ......... 351/205–206, 351/221; 354/62
See application file for complete search history.

(56) References Cited

U.S. PATENT DOCUMENTS

| 4,900,144 | A | * | 2/1990 | Kobayashi ................... 351/206 |
| 5,506,634 | A | | 4/1996 | Wei et al. |
| 5,537,162 | A | | 7/1996 | Hellmuth et al. |
| 5,568,208 | A | * | 10/1996 | Van de Velde ............... 351/221 |
| 5,975,697 | A | * | 11/1999 | Podoleanu et al. .......... 351/206 |
| 6,004,314 | A | | 12/1999 | Wei et al. |
| 6,826,359 | B1 | | 11/2004 | Takeda |
| 2003/0218755 | A1 | | 11/2003 | Wei et al. |
| 2004/0036838 | A1 | | 2/2004 | Podoleanu et al. |
| 2007/0002277 | A1 | * | 1/2007 | Hanebuchi ................... 351/206 |
| 2007/0070295 | A1 | * | 3/2007 | Tsukada et al. ............. 351/206 |

FOREIGN PATENT DOCUMENTS

| JP | 2002-306416 | 10/2002 |
| JP | 2003-000543 | 1/2003 |
| JP | 2004-350849 | 12/2004 |
| JP | 2005-241464 | 9/2005 |
| WO | WO 2005/077257 | 8/2005 |
| WO | WO 2006/052479 | 5/2006 |

* cited by examiner

*Primary Examiner*—Scott J Sugarman
*Assistant Examiner*—Dawayne A Pinkney
(74) *Attorney, Agent, or Firm*—Edwards Angell Palmer & Dodge LLP

(57) ABSTRACT

A fundus observation device which can simultaneously capture both surface images and tomographic images of the fundus oculi is provided. The fundus observation device 1 has a fundus camera unit 1A, an OCT unit 150, and an arithmetic and control unit 200. The fundus camera unit 1A has an illuminating optical system 100 and an imaging optical system 120. The arithmetic and control unit 200 forms the surface image of fundus oculi Ef based on signals from fundus camera unit 1A. The OCT unit 150 divides low coherence light LO into the signal light LS and the reference light LR, and detects the interference light LC that can be obtained from the signal light LS passing through fundus oculi Ef and the reference light LR passing through reference mirror 174. The arithmetic and control unit 200 forms tomographic images of fundus oculi Ef based on these detecting results. A Dichroic mirror 134 combines the optical path of the signal light LS toward fundus oculi Ef into the optical path for imaging of the imaging optical system 120, and separates the optical path of the signal light LS towards fundus oculi Ef from the optical path for imaging.

16 Claims, 10 Drawing Sheets

(A)

(B)

FUNDUS OBSERVATION DEVICE

BACKGROUND OF THE INVENTION

1. Field of the Invention

The present invention relates to a fundus observation device, for observing the state of the fundus oculi of an eye to be examined.

2. Description of the Related Art

As a fundus observation device, conventionally a fundus camera has been widely used. FIG. 9 shows one example of the appearance of a conventional fundus camera in general, and FIG. 10 shows one example of an optical system composition to be internally accommodated therein (e.g. JP Patent laid-open No. 2004-350849). Furthermore, "observation" is intended to include at least a case in which produced fundus images are observed (fundus observations with the naked eye may be included).

First, referring to FIG. 9, an explanation is made regarding the appearance of a conventional fundus camera 1000. This fundus camera is provided with a platform 3 mounted on a base 2 slidably in the front and rear, right and left (horizontal direction) directions. On this platform 3, an operation panel 3a and a control lever 4 are installed for an examiner to conduct various operations.

The examiner may place the platform 3 on the base 2 to be moved 3-dimensionally by operating the control lever 4. On the top of the control lever 4, an operation button 4a is installed to be pressed down to form fundus oculi images.

On the base 2, a post 5 is installed standing upwards. On the post 5, a jaw rest 6 where the jaw of a patient is to be rested and an external fixation lamp 7 as a light source for fixing an eye to be examined E are provided.

On the platform 3, a main body part 8 is installed to accommodate various optical systems or control systems of the fundus camera 1000. Furthermore, the control system may be installed inside the base 2 or the platform, etc., or in an external device such as a computer, etc. connected to the fundus camera 1000.

On the side of the eye to be examined E of the main body part 8 (the left side of the page in FIG. 9), an objective lens part 8a disposed opposite the eye to be examined E is installed. Also, on the examiner's side of the main body part 8 (the right side of the page in FIG. 9), an objective lens part 8b for observing the fundus oculi of the eye to be examined E with the naked is installed.

Furthermore, connected to the main body part 8 is a still camera 9 for producing a still image of a fundus oculi of the eye to be examined E and an imaging device 10 such as a TV camera, etc. for producing still images or moving images of a fundus oculi. The still camera 9 and the imaging device 10 are formed removably with respect to the main body part 8.

As a still camera 9, in accordance with various conditions such as the purpose of an examination or the saving method of produced images, etc., a digital camera equipped with imaging elements such as CCD (Charge Coupled Device) or CMOS (Complementary Metal Oxide Semiconductor), a film camera, and an instant camera, etc. may interchangeably be used when it is appropriate. The main body part 8 is equipped with a mounting part 8c for interchangeably mounting such a still camera 9.

If the still camera 9 or the imaging device 10 is for taking digital images, the image data of the produced fundus image may be sent to a device such as a computer, etc. connected to the fundus camera 1000 and be observed as a fundus image by being displayed on the display. Also, the image data in an image storing device connected to the fundus camera 1000 can be sent to compile a database and be used as electronic data for creating medical charts, etc.

Furthermore, on the examiner's side of the main body part 8, a touch panel monitor 11 is installed. On this touch panel monitor 11, fundus images of the eye to be examined E created based on the picture signals output from the still camera 9 (a digital method thereof) or the imaging device 10 are displayed. Moreover, on the touch panel monitor 11, the xy coordinate system with the center of the screen as the origin is displayed overlapped with a fundus image. When the screen is touched by the examiner, the coordinate value corresponding to the touched position is displayed.

Next, referring to FIG. 10, a composition of an optical system of the fundus camera 1000 is described. The fundus camera 1000 is provided with an illuminating optical system 100 to light the fundus oculi Ef of an eye to be examined E, an imaging optical system 120 to guide the fundus reflection light of the illumination light to the eyepiece part 8b, a still camera 9, and an imaging device 10.

The illuminating optical system 100 comprises: an observation light source 101, a condenser lens 102, an imaging light source 103, a condenser lens 104, an exciter filter 105 and 106, a ring transparent plate 107, a mirror 108, a liquid crystal display (LCD) 109, an illumination diaphragm 110, a relay lens 111, an aperture mirror 112, and an objective lens 113.

The observation light source 101 consists of a halogen lamp, etc. and emits fixed light (continuous light) for observing the fundus. The condenser lens 102 is an optical element that converges the fixed light (observation illumination light) emitted by the observation light source 101 and substantially evenly irradiates the observation illumination light to the fundus oculi.

The imaging light source 103 consists of a xenon lamp, etc. to be flashed when producing fundus oculi Ef images. The condenser lens 104 is an optical element that converges the flash light (imaging illumination light) emitted by the imaging light source 103 and irradiates the fundus oculi Ef evenly with the imaging illumination light.

The exciter filters 105 and 106 are the filters to be used when fluorography of ocular fundus images of a fundus oculi Ef takes a place. The exciter filters 105 and 106 respectively can be inserted and/or removed on the optical path by a drive mechanism such as a solenoid, etc. The exciter filter 105 is disposed on the optical path in the event of FAG (fluorescein angiography). Whereas, the exciter filter 106 is disposed on the optical path in the event of ICG (indocyanine green angiography). Furthermore, when color images are being obtained, both exciter filters 105 and 106 are retracted from the optical path.

The ring transparent plate 107 is disposed in a conjugating location with a pupil of the eye to be examined E, and is equipped with a ring transparent part 107a taking an optical axis of the illuminating optical system 100 as a center. The mirror 108 reflects the illumination light emitted by the observation light source 101 or by the imaging light source 103 in the direction of the optical axis of the imaging optical system 120. The LCD 109 displays a fixation target (not illustrated) for fixing the eye to be examined E.

The illumination diaphragm 110 is a diaphragm member to shut out a part of the illumination light for flare prevention, etc. This illumination diaphragm 110 is composed movably in the light axial direction of the illuminating optical system 100, and is thus capable of changing the illuminating region of the fundus oculi Ef.

The aperture mirror 112 is an optical element to combine an optical axis of the illuminating optical system 100 and an optical axis of the imaging optical system 120. In the center region of the aperture mirror 112 an aperture part 112*a* is opened. The light axis of the illuminating optical system 100 and the light axis of the imaging optical system 120 are to be crossed at a substantially central location of this aperture part 112*a*. The objective lens 113 is installed in the objective lens part 8*a* of the main body part 8.

The illuminating optical system 100 having such a composition illuminates a fundus oculi Ef in the following manner. First, the observation illumination light is output when the observation light source 101 is lit during fundus observation. This observation illumination light irradiates the ring transparent plate 107 through the condenser lenses 102 and 104. (The exciter filters 105 and 106 are removed from the optical path.) The light passed through the ring transparent part 107*a* of the ring transparent plate 107 is reflected by the mirror 108 and is reflected along the optical axial direction of the imaging optical system 120 due to the aperture mirror 112 through the LCD 109, the illumination diaphragm 110 and the relay lens 111. The observing illumination light reflected by the aperture mirror 112 advances in the optical axial direction of the imaging optical system 120 and is converged by the objective lens 113, to be made incident onto the eye to be examined E, and illuminates the fundus oculi Ef.

Then, the ring transparent plate 107 is disposed in a conjugating location with the pupil of the eye to be examined E, and on the pupil a ring shaped image of the entering observation illumination light is formed. The fundus reflection light of the entered observation illumination light is to be emitted from the eye to be examined E through a central dark part of the ring image on the pupil. As described, it is to protect the effect of observing illumination light entering the eye to be examined E with respect to the fundus reflection light of the observing illumination light.

On the other hand, when imaging the fundus oculi Ef, flush light is emitted from the imaging light source 103 and the imaging illumination light is irradiated onto the fundus oculi Ef through the same path. In the event of photofluographing, either the exciter filter 105 or the exciter filter 106 is disposed selectively on the optical path depending on whether FAG imaging or ICG imaging is required.

Whereas, imaging optical system 120 comprises: an objective lens 113, an aperture mirror 112 (an aperture part 112*a* thereof), an imaging diaphragm 121, a barrier filter 122 and 123, a variable magnifying lens 124, a relay lens 125, an imaging lens 126, a quick return mirror 127 and an imaging media 9*a*. Herein, the imaging media 9*a* is an arbitrary imaging media (image pick-up elements such as CCD, camera film, instant film, etc.) used for a still camera 9.

The fundus reflection light of the illumination light, emitted through the central dark part of the ring shaped image formed on the pupil from the eye to be examined E, enters the imaging diaphragm 121 through the aperture part 112*a* of the aperture mirror 112. The aperture mirror 112 reflects cornea reflection light of the illumination light and acts so as not to mix the cornea reflection light into the fundus reflection light made incident onto the imaging diaphragm 121. As a result, the generation of flare on the observation images and/or produced images is prevented.

The imaging diaphragm 121 is a plate shaped member at which plural circular light transparent parts of different sizes are formed. The plural light transparent parts constitute different diaphragms with different diaphragm values (F value), and are to be disposed alternatively on the optical path by a drive mechanism (not illustrated herein).

The barrier filters 122 and 123 can be inserted and/or removed on the optical path by a drive mechanism such as a solenoid, etc. In the event of FAG imaging, the barrier filter 122 is disposed on the optical path while in the event of ICG imaging the barrier filter 123 is inserted onto the optical path. Furthermore, when producing color images the barrier filters 122 and 123 are to be retracted from the optical path.

The variable magnifying lens 124 is to be movable in the light axial direction of the imaging optical system 120 by a drive mechanism (not illustrated herein). This makes it possible to change the magnifying ratio of an observation and the magnifying ratio in imaging, and to focus images of a fundus oculi. The imaging lens 126 is a lens to form an image of the fundus reflection light from an eye to be examined E on the imaging media 9*a*.

The quick return mirror 127 is disposed rotatably around a rotary shaft 127*a* by a drive mechanism not illustrated herein. In the event of imaging a fundus oculi Ef with the still camera 9, the fundus reflection light is supposed to be guided to the imaging media 9*a* by springing up the quick return mirror 127 that is obliquely mounted on the optical path. Whereas, in the event of imaging a fundus oculi with an imaging device 10 or of observing the fundus oculi with the naked eye of the examiner, the quick return mirror 127 is to be obliquely mounted on the optical path to upwardly reflect the fundus reflection light.

The imaging optical system 120 is further provided with a field lens (eye vision lens) 128 for guiding the fundus reflection light reflected by the quick return mirror 127, a switching mirror 129, an eyepiece 130, a relay lens 131, a reflection mirror 132, an imaging lens 133 and an image pick up element 10*a*. The image pick up element 10*a* is an image pick up element such as CCD, etc. installed internally in the imaging device 10. On the touch panel monitor 11 a fundus oculi image Ef' imaged by the image pick up element 10*a* is be displayed.

The switching mirror 129 is to be rotatable around the rotary shaft 129*a* as well as the quick return mirror 127. This switching mirror 129 is obliquely disposed on the optical path during observation with the naked eye and guides reflected light on the fundus oculi to the eyepiece 130.

Also, when a fundus image is formed by the imaging device 10, the switching mirror 129 is retracted from the optical path, and the fundus reflection light is guided toward an image pick-up element 10*a*. In this case, the fundus reflection light is directed toward a relay lens 131, is reflected by the mirror 132, and is formed on the image pick-up element 10*a* by the imaging lens 133.

Such a fundus camera 1000 is a fundus observation apparatus to be used for observing the state of the surface of a fundus oculi Ef, that is, the retina. In other words, a fundus camera 1000 is a fundus observation apparatus to obtain a 2-dimensional fundus oculi image when it sees the fundus oculi Ef from the corneal direction onto the eye to be examined E. On the other hand, in the deep layer of retina tissues such as where the choroidea or sclera exist, technology for observing these deep layer tissues has been desired, but, in recent years, devices for observing these deep layer tissues have been practically implemented (e.g. JP Patent laid-open No. 2003-00543, JP Patent laid-open No. 2005-241464).

The fundus observation apparatus disclosed in JP Patent laid-open No. 2003-00543 and JP Patent laid-open No. 2005-241464 are devices to which so called OCT (Optical Coherence Tomography) technology is applied. With such fundus observation devices, low coherence light is split into two, one of which (signal light) is guided to a fundus oculi and the other one (reference light) is guided to a given reference object, while at the same time this is a device to form tomographic images of the surface and the deep layer tissue of a fundus oculi, and to form the 3-dimensional image from the tomographic images, by detecting and analyzing the interference light obtained by overlaying the signal light that has passed through the fundus oculi and the reference light that has been reflected by the reference object. Such images are called light CT images or OCT images, etc.

In order to capture the state of a fundus oculi (presence/absence of a disease or the progressing state, the degree of a therapy effect or a recovery state, etc.) in detail, it is desirable to consider both the state of fundus surface (retina) and the state of deep layer tissues (choroidea or sclera). However, by just observing an image .of the fundus surface obtained from a fundus camera, it is difficult to capture the state of the deep layer tissues in detail, while, with tomographic images of the fundus oculi obtained from an optical image measuring device, it was difficult to capture the detailed state of the fundus surface or the entire retina.

Furthermore, in order to determine the state of fundus oculi comprehensively, it is considered to be desirable to determine the state of a disease by taking both the state of the retina and the state of deep layer tissues into consideration. That is, in order to improve the accuracy in determining the condition of a disease, etc., it is desirable to refer to more information and also to refer to information from multiple angles.

For this purpose, it is desirable to use a fundus observation device which permits to obtain both a fundus image from a fundus camera and a fundus image from an optical image measuring device. In particular, if it is possible to simultaneously produce both images, it permits to observe the condition of the fundus by another fundus image in imaging one fundus image.

However, with conventional fundus observation devices, it was difficult to capture both a 2-dimensional surface image of the fundus of an eye to be examined by a fundus camera, a tomographic image of the fundus, and a 3-dimensional image by an optical image measuring device. In particular, it was difficult to capture both fundus images at the same time.

Also, to form a fundus observing device for capturing both a fundus image by a fundus camera and a fundus image by an optical image measuring device, it is desirable to irradiate the signal light through the optical system of a fundus camera to the fundus and to overlap with the reference light by guiding the signal light directed toward the fundus. That is, by guiding the signal light by the optical system of a fundus camera, the tomographic images of the same position on the fundus oculi as the image by a fundus camera can be captured and the condition of the position on the fundus oculi can be observed in detail.

However, when a composition is adapted in which the signal light is guided by the optical system of a fundus camera, the signal light passes through more optical elements than a conventional optical image measuring device. Thus, due to the effect of the dispersion of these optical elements, the interference efficiency of the signal light and the reference light decreases such that sufficient intensity interference light may not be generated. Therefore, when the image is formed based on the deficient intensity interference light, the OCT image is of low contrast and is unclear, as with a conventional optical image measuring device.

Furthermore, with conventional optical image measuring devices, the difference in the effect between both the signal light and the reference light is compensated by the image processing. But for both fundus images by a fundus camera and fundus images by an optical image measuring device of an adequate fundus observing device, there is a large difference between the number of optical elements passing through the signal light and the number of optical elements passing through the reference light such that there is a difference between the effect of dispersion to the signal light and the effect of dispersion to the reference light, and correction by the image processing may be insufficient.

The present invention is intended to solve such problems by capturing both the image of the surface of the fundus oculi and the tomographic images of the fundus oculi, and it particularly intends to provide a fundus observation device capable of simultaneously capturing both of these fundus images.

Further, the present invention can capture both the image of the surface of the fundus oculi and the tomographic images of the fundus oculi, with a further purpose of providing a fundus observing device capable of controlling the decrease in interference efficiency of both the signal light and the reference light by optical image measurement.

SUMMARY OF THE INVENTION

In order to achieve the above purpose, the first embodiment is constructed as follows: A fundus observation device comprising: a first image forming means having an illuminating optical system for emitting illumination light onto fundus oculi of an eye to be examined and an imaging optical system for detecting the illumination light passing through said fundus oculi by the first detecting means, wherein the first image forming means forms a 2-dimensional image of the surface of said fundus oculi based on the detection results by said first detecting means; and a second image forming means having a light source which outputs light of a wavelength which is different from said illumination light, an interference optical generating means splitting said light output from said light source into the signal light directed towards said fundus oculi and the reference light directed towards a reference object and generating interference light by overlapping the signal light passing through said fundus oculi and the reference light passing through said reference object, along with a second detecting means for detecting said interference light generated, forming tomographic images of said fundus oculi based on the detected results by said second detecting means; and an optical path combination and separation means for combining the optical path for imaging formed by said imaging optical system and the optical path of a signal light directed toward said fundus oculi and separating said optical path for imaging from the optical path of the signal light toward said fundus oculi; wherein said signal light combined with said optical path for imaging irradiates onto said fundus oculi through said optical path for imaging, and said signal light separated from said optical path for imaging overlaps said reference light by said interference light generating means.

Also, the second embodiment is constructed as follows: A fundus observation device according to the first embodiment, wherein said interference optical generating means further comprises a dispersion assignment means for assigning dispersion to said reference light.

Also, the third embodiment is constructed as follows: A fundus observation device according to the second embodiment, wherein said dispersion assignment means assigns to said reference light a dispersion amount generally equal to the dispersion amount assigned to said signal light during the time from said splitting to said overlapping by said interference light generating means.

Also, the fourth embodiment is constructed as follows: A fundus observation device according to the first embodiment, wherein the total value of the dispersion amount of plural optical elements through which said signal light passes during the time from said splitting to said overlapping by said interference light generating means is generally equal to the total value of the dispersion amount of plural optical elements through which said reference light passes during the time from said splitting to said overlapping by said interference light generating means.

Also, the fifth embodiment is constructed as follows: A fundus observation device according to the fourth embodiment, wherein the dispersion amount that said signal light is assigned by air during the time from said splitting to said overlapping by said interference light generating means is generally equal to the dispersion amount that said reference light is assigned by air during the time from said splitting to said overlapping by said interference light generating means Effects of the Invention The fundus observation device related to the first embodiment comprises a first image forming means for forming 2-dimensional images of the surface of the fundus oculi and a second image forming means for forming tomographic images of the fundus oculi. The imaging optical system of the first image forming means forms the optical path for imaging. The second image forming means generates the interference light by overlapping the signal light passing through the fundus oculi to the reference light, and forms tomographic images of the fundus oculi based on this interference light.

Optical combination and separation means operates to combine the optical path of the signal light toward the fundus oculi and the optical path for imaging. The signal light irradiates onto the fundus oculi through this optical path for imaging. Also, optical combination and separation means operates to separate the signal light toward the fundus oculi from the optical path for imaging. The separated signal light generates the interference light by overlapping the reference light.

Such optical combination and separation means permits to capture both 2-dimensional images of the surface of the fundus oculi and tomographic images of the fundus oculi. In particular, when the illumination light from the first image forming means irradiates and the illumination from the signal light by the second image forming means irradiate simultaneously, each light through the fundus oculi is separated by the optical path combination and separation means, and each light is detected so that the image is formed. Therefore, the fundus observation device related to the present invention allows both 2-dimensional images of the surface of the fundus oculi and tomographic images of the fundus oculi to be captured simultaneously.

Additionally, by the fundus observation device according to the second embodiment, because it has dispersion assignment means for allowing dispersion of the reference light, it can reimburse at least one part of the dispersion assignment to the signal light when the optical path for imaging passes through. As a result, it can control the decrease in interference efficiency for both the signal light and the reference light.

In particular, the fundus observation device according to the third embodiment, during the time from splitting by the interference light generating means through the fundus oculi to overlapping with the reference light, can comprise the dispersion assignment means for allowing dispersion assignment to the signal light and the dispersion which substantially equals the reference light, so it is almost equal to each dispersion assignment for overlapping both the signal light and the reference light on each other. As a result, it can interfere with the signal light and the reference light with high interference efficiency, allowing it to capture clear and highly accurate tomographic images (OCT images).

Moreover, by the fundus observation device according to the fourth embodiment, it is possible for the total value of the dispersion of several optical elements through which the signal light passes during the time from splitting by interference light generating means to overlapping with the reference light through the fundus oculi and the total value of the dispersion of several optical elements through the reference light to be substantially equal, and therefore, it is almost equal to the dispersion allowing both the signal light and the reference light to overlap each other, allowing it to interfere with both the signal light and the reference light with high interference efficiency.

Also, by the fundus observation device according to the fifth embodiment, it is possible that the total value of the dispersion assignment of the signal light by air during the time from splitting by interference light generating means to overlapping with the reference light through the fundus oculi and the total value of the dispersion assignment of the reference light by air during the time from splitting by the interference light generating means to overlapping with the reference light through the fundus oculi are substantially equal, and therefore, it can be closer the dispersion assigning both signal light and the reference light to overlap each other, making it possible to better control the decrease in the interference efficiency of both the signal light and the reference light.

BRIRF DESCRIPTION OF THE DRAWINGS

Figure 6:
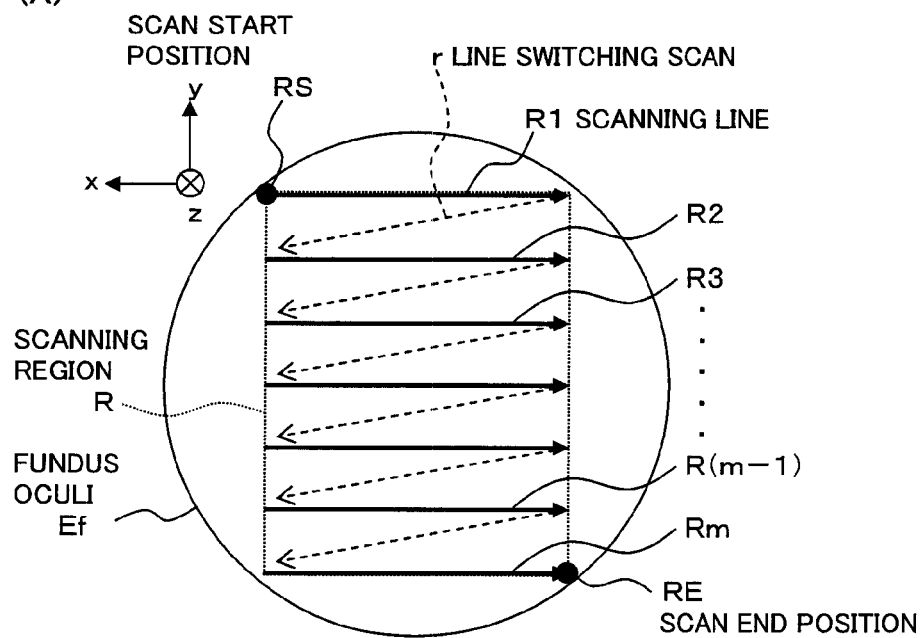
Figure 6:
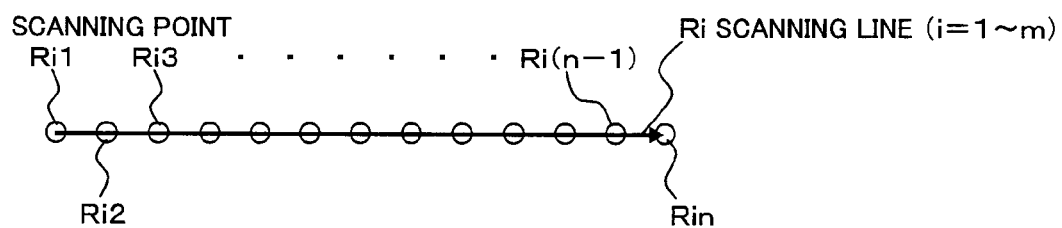

FIG. 6 is a schematic diagram representing one example of scanning features of signal light in a favorable embodiment of the fundus observation device related to the present invention. FIG. 6(A) represents one example of the scanning features of signal light when a fundus oculi is seen from the incident side of the signal light with respect to an eye to be examined. In addition, FIG. 6(B) represents one example of arrangement features of scanning points of each scanning line.

Figure 7:
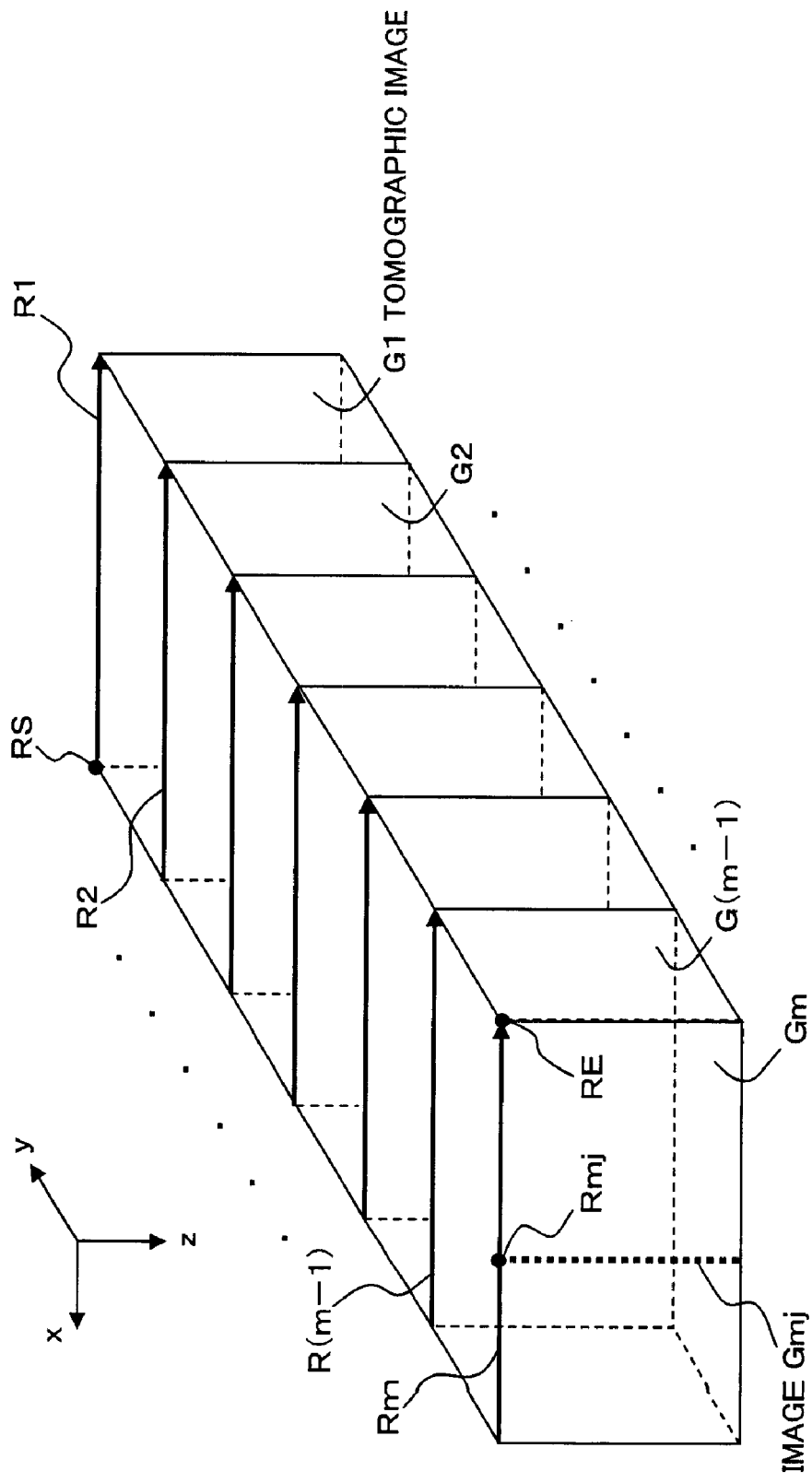

FIG. 7 is a schematic diagram representing one example of the scanning features of signal light and tomographic image features formed along each scanning line in a favorable embodiment of the fundus observation device related to the present invention.

Figure 8:
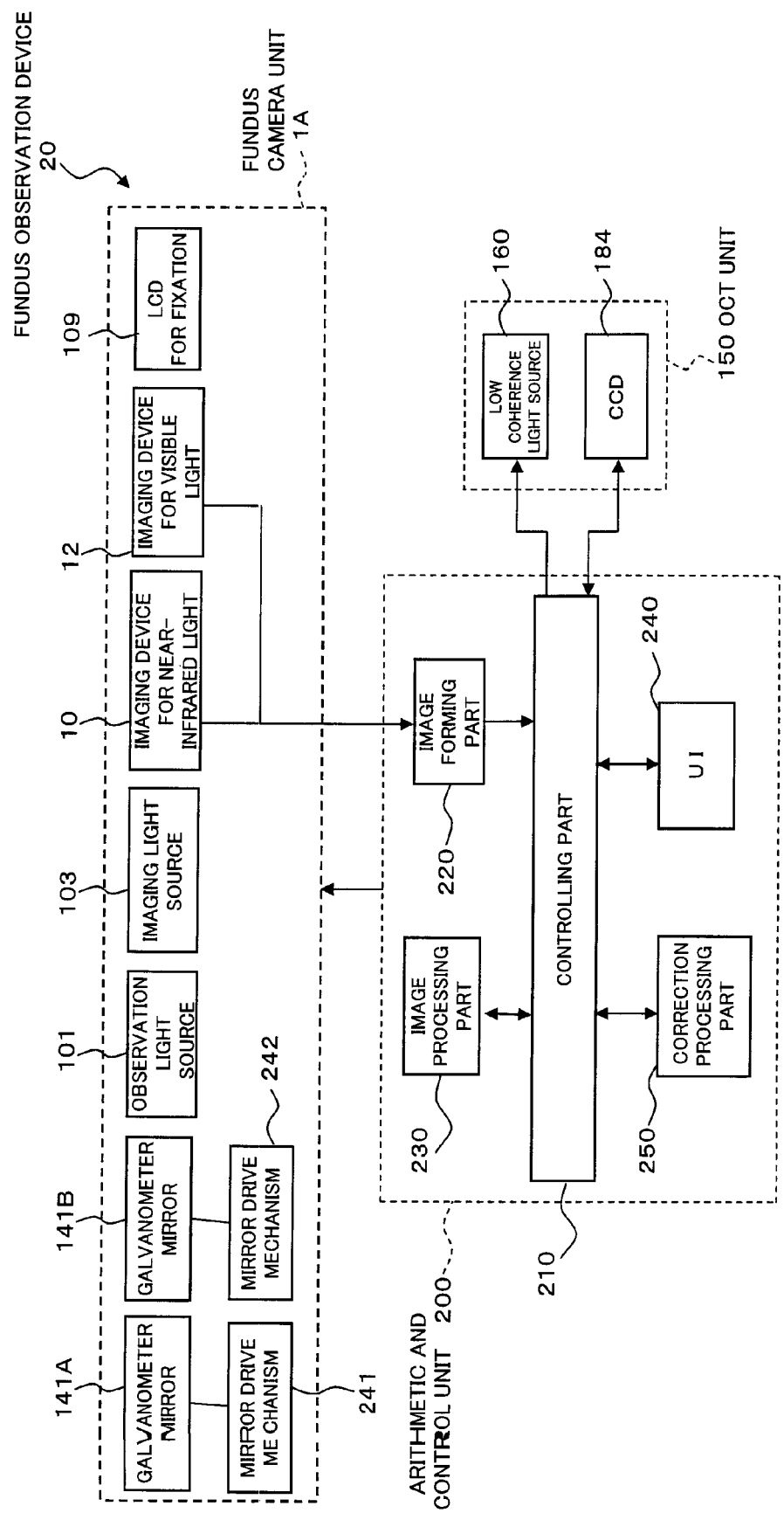

FIG. 8 is a schematic block diagram representing one constitutional example of a control system in a favorable embodiment of the fundus observation device related to the present invention.

Figure 9:
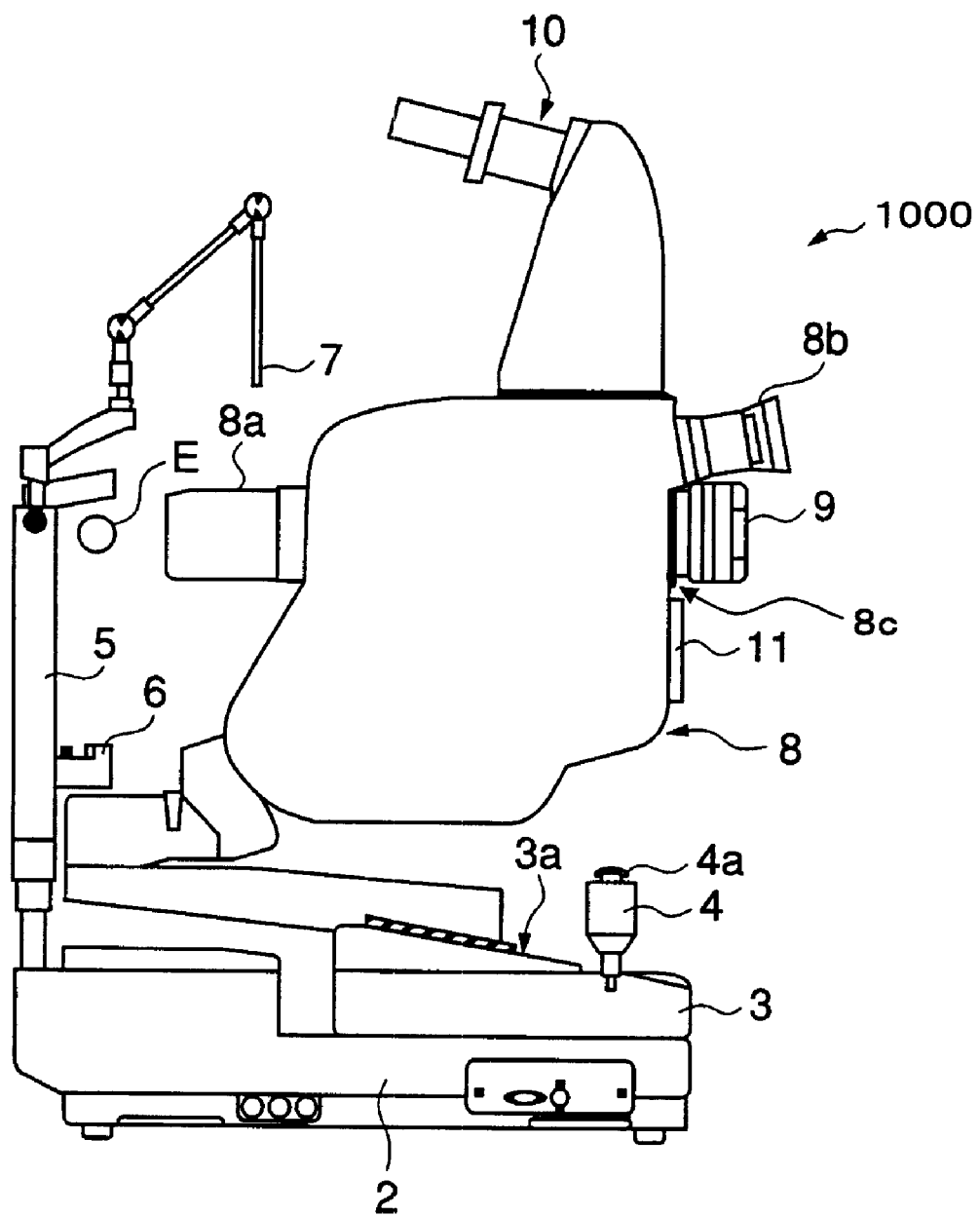

FIG. 9 is a schematic side view representing an appearance constitution of a conventional fundus observation device (fundus camera).

Figure 10:
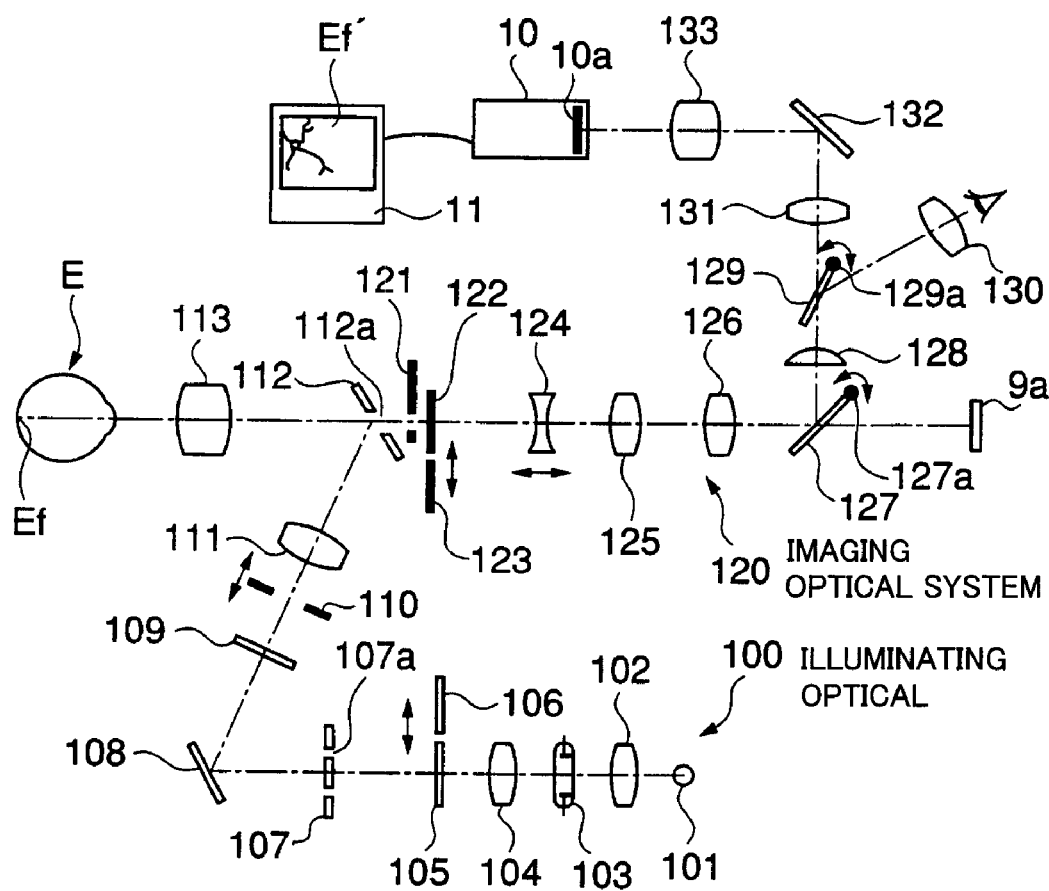

FIG. 10 is a schematic diagram representing one example of an internal constitution (an optical system constitution) of a conventional fundus observation device (fundus camera).

DETAILED DESCRIPTION OF THE REFERENCE EMBODIMENTS

One example of favorable embodiments of a fundus observation device related to the present invention is described in detail referring to figures. Furthermore, for constitutional parts that are the same as conventional ones, the same numeric symbols used in FIG. 9 and FIG. 10 are used.

Embodiment 1

Figure 1:
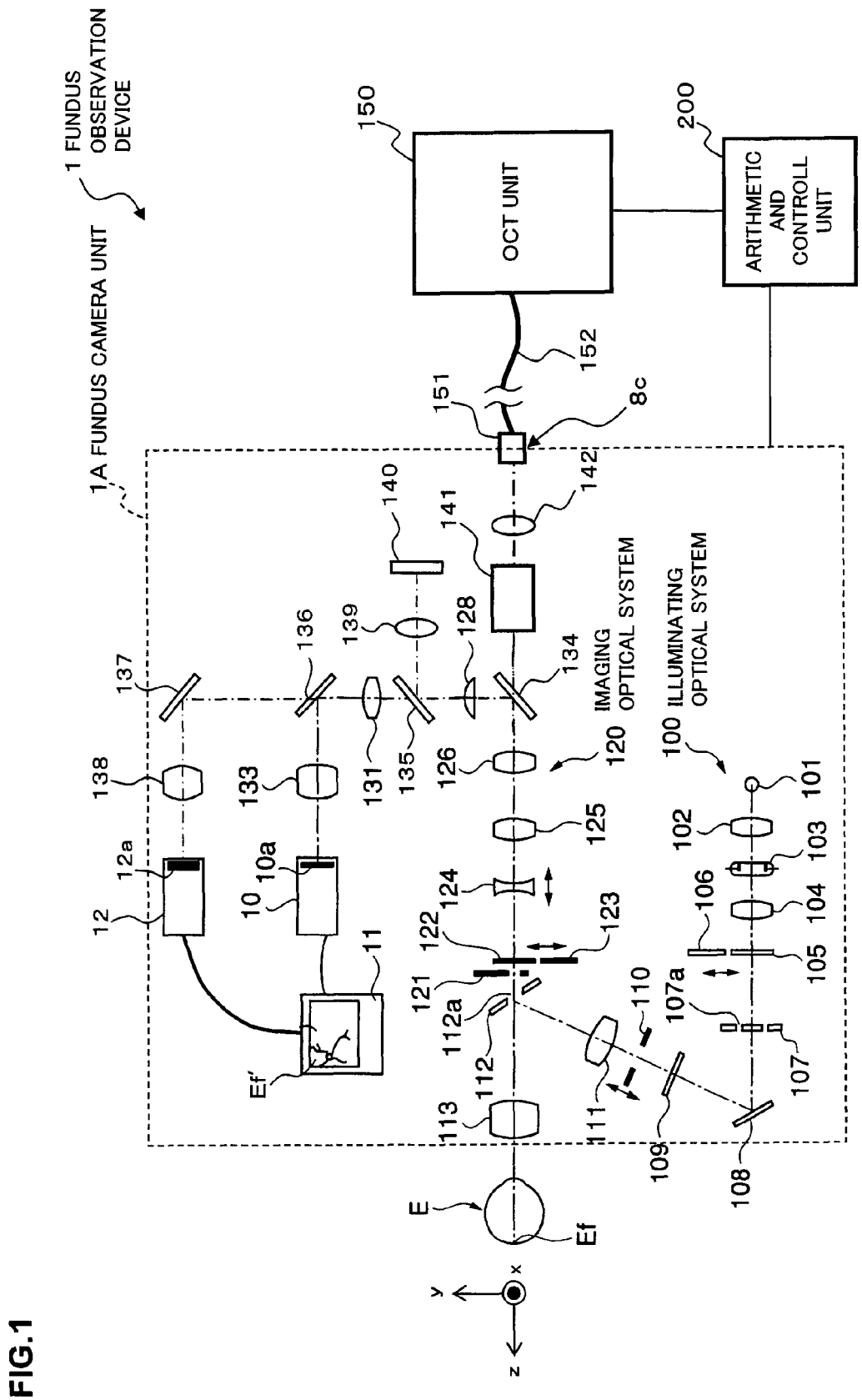
FIG. 1 is a schematic diagram representing one example of the entire constitution in a favorable embodiment of the fundus observation device related to the present invention.
Figure 2:
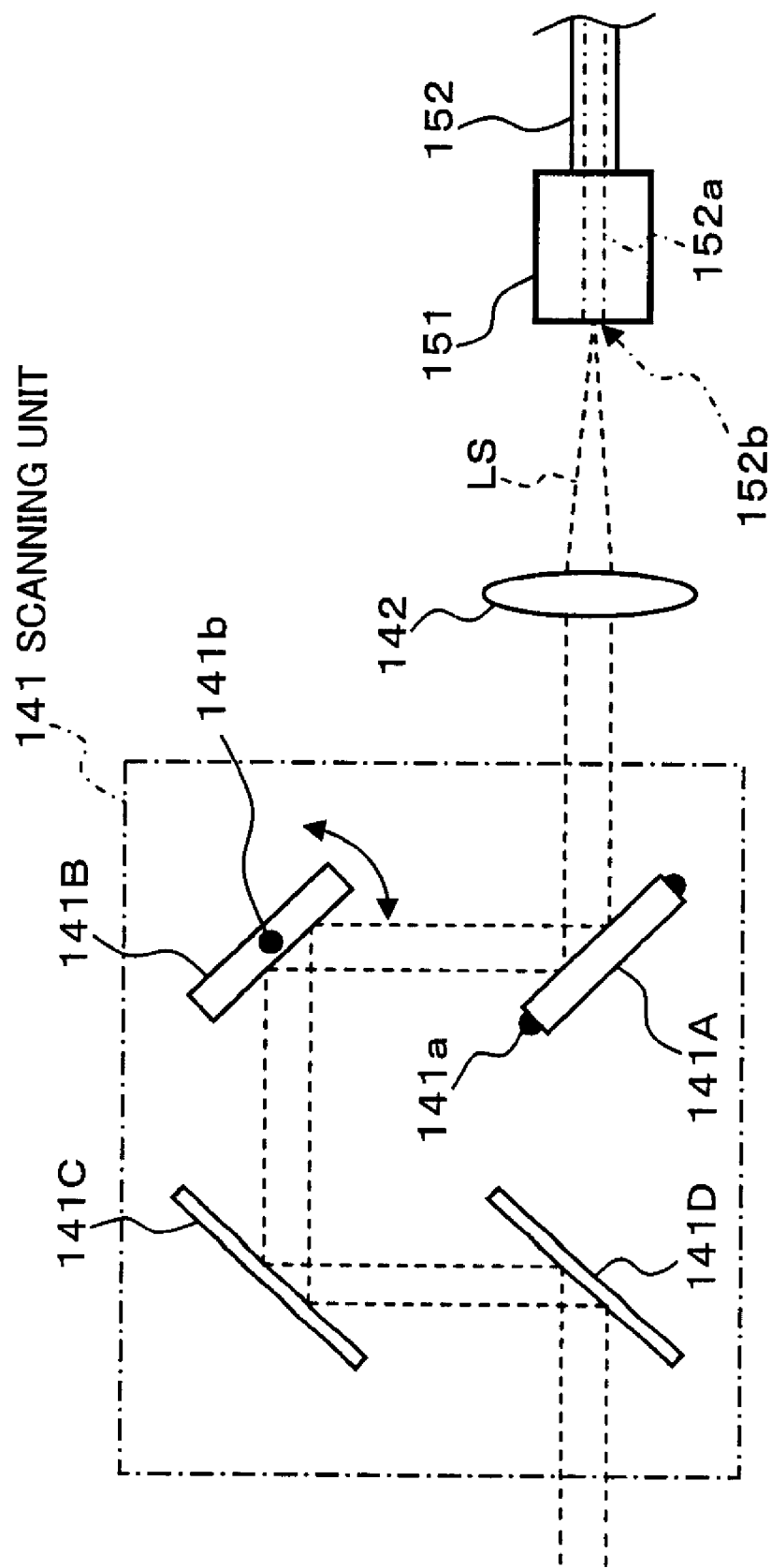
FIG. 2 is a schematic diagram representing one costitutional example of a scanning unit installed in a fundus camera unit in a favorable embodiment of the fundus observation device related to the present invention.
Figure 3:
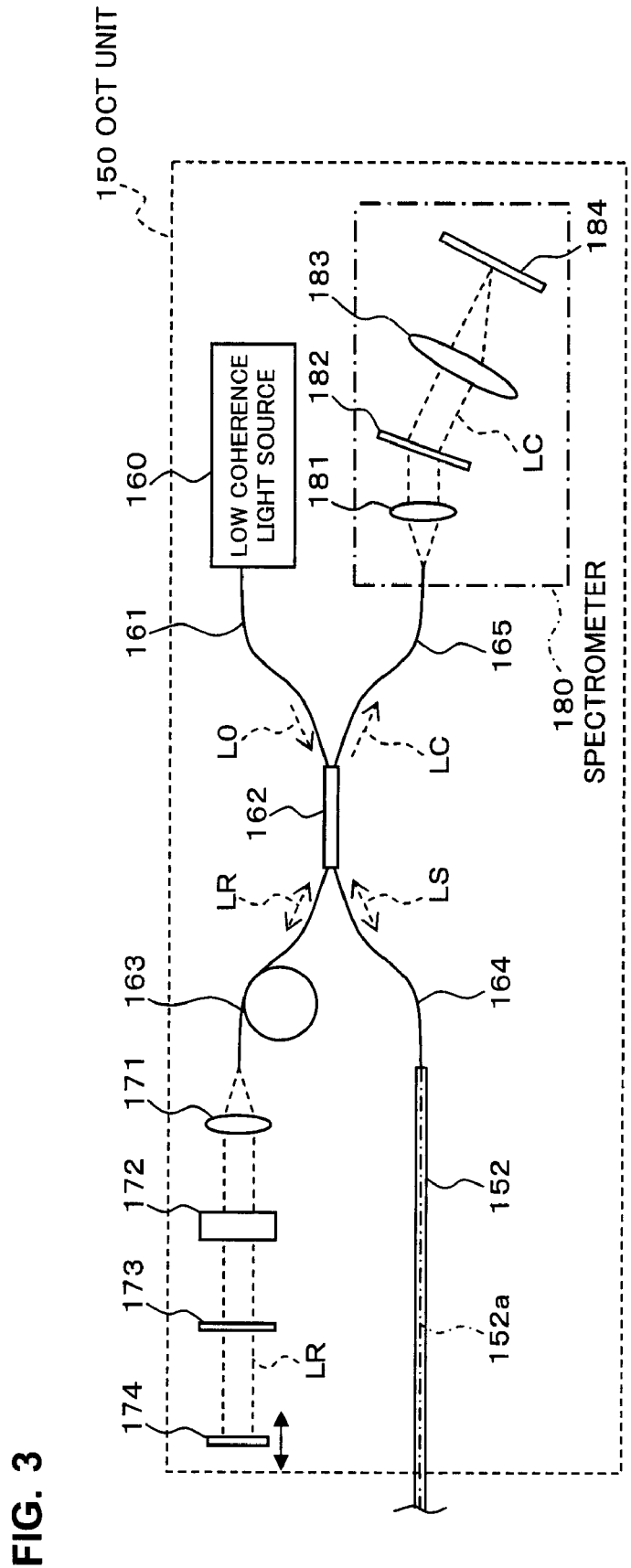
FIG. 3 is a schematic diagram representing one costitutional example of an OCT unit in a favorable embodiment of the fundus observation device related to the present invention.
Figure 4:
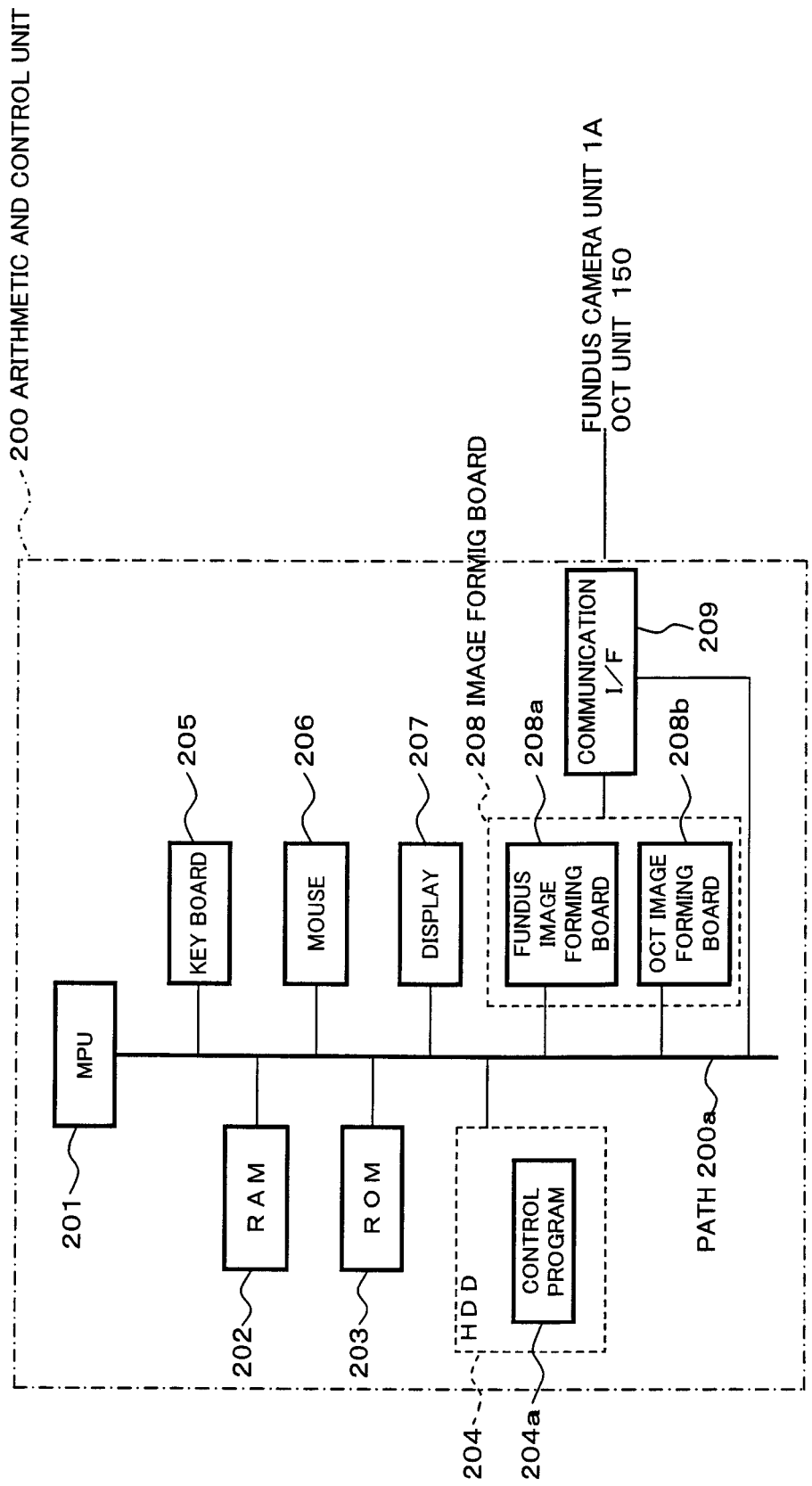
FIG. 4 is a schematic block diagram representing one example of hardware configurations of an arithmetic and control unit in a favorable embodiment of the fundus observation device related to the present invention.
Figure 5:
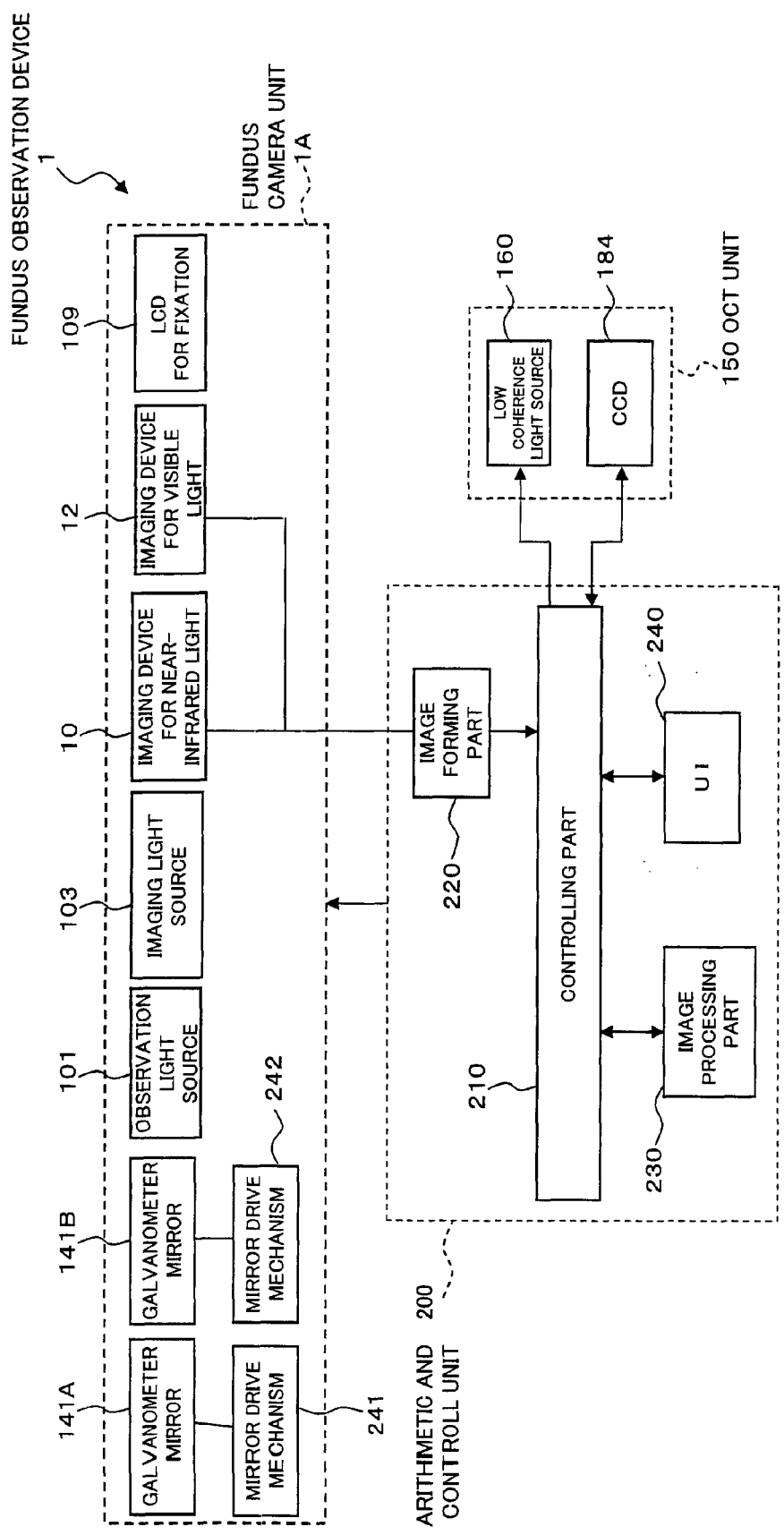
FIG. 5 is a schematic block diagram representing one costitutional example of a control system in a favorable embodiment of the fundus observation device related to the present invention.

First, by referring to FIGS. 1 through 5, the constitution of Embodiment 1 of the fundus observation device related to the present invention is described. FIG. 1 shows the entire constitution of the fundus observation device 1 related to the present invention. FIG. 2 shows a constitution of a scanning unit 141 in a fundus camera unit 1A. FIG. 3 shows a constitution of an OCT unit 150. FIG. 4 shows a hardware configuration of an arithmetic and control unit 200. FIG. 5 shows a configuration of a control system of the fundus observation unit 1.

The Entire Constitution

As shown in FIG. 1, the fundus observation device 1 is comprised of a fundus camera unit 1A that functions as a fundus camera, an OCT unit 150 accommodating the optical system of an optical image measuring device (OCT device), and an arithmetic and control unit 200 that executes various control processes, etc.

This fundus camera unit 1A is a component of one embodiment of the "first image forming means" with the arithmetic and control unit 200. Also, the OCT unit 150 is a component of one embodiment of the "second image forming means" with the arithmetic and control unit 200. Further, this "second image forming means" also includes each optical element through the signal light such as a scan unit 141 provided in the fundus camera unit 1A, etc.

To the OCT unit 150, one end of a connection line 152 is attached. To the other end of this connection line 152, a connector part 151 is attached. This connector part 151 is attached to a mounting part 8c shown in FIG. 9. Furthermore, a conductive optical fiber runs through the inside of the connection line 152. The OCT unit 150 and the fundus camera unit 1A are optically connected through the connection line 152. The costitution details of the OCT unit 150 are to be described later referring to FIG. 3.

Constitution of Fundus Camera Unit

The fundus camera unit 1 A has substantially the same appearance as the conventional fundus camera 1000 shown in FIG. 9. Furthermore, as in the conventional optical system shown in FIG. 10, the fundus camera unit 1A is provided with an illuminating optical system 100 to light a fundus oculi Ef of an eye to be examined E, and an imaging optical system 120 for guiding the fundus reflection light of the illumination light to an eyepiece 8b, an imaging device 10, and an OCT unit 150.

In addition, although the details are to be described later, an imaging device 10 in an imaging optical system 120 of the present embodiment is used for detecting the illumination light with a wavelength in the near-infrared region. Furthermore, in this imaging optical system 120, an imaging device 12 for detecting the illumination light with wavelength in the visible region is provided separately. In addition, in this imaging optical system 120, it can guide the signal light from the OCT unit 150 to the fundus oculi Ef and the signal light through the fundus oculi Ef to the OCT unit 150.

Also, the illuminating optical system 100 is comprised as in conventional ones including: an observation light source 101, a condenser lens 102, an imaging light source 103, a condenser lens 104, an exciter filter 105 and 106, a ring transparent plate 107, a mirror 108, an LCD 109, an illumination diaphragm 110, a relay lens 111, an aperture mirror 112, and an objective lens 113.

The observation light source 101 outputs the illumination light of a wavelength in the visible region included within about 400 nm to 700 nm. This observation light source 101 is the equivalent of one example of the "visible light source" of the present invention. Furthermore, the imaging light source 103 outputs the illumination light of the wavelength in the near-infrared region included within about 700 nm to 800 nm. The near-infrared light output from this imaging light source 103 is provided shorter than the wavelength of the light used by the OCT unit 150 (to be described later).

At the same time, the imaging optical system 120 comprises: an objective lens 113, an aperture mirror 112 (aperture part 112a thereof), an imaging diaphragm 121, a barrier filter 122 and 123, a variable magnifying lens 124, a relay lens 125, an imaging lens 126, a dichroic mirror 134, a field lens (eye vision lens) 128, a half mirror 135, a relay lens 131, a dichroic mirror 136, an imaging lens 133, an imaging device 10 (an image pick-up element 10a), a reflection mirror 137, an imaging lens 138, an imaging device 12 (an image pick-up element 12a), and a lens 139 and LCD (Liquid crystal Display) 140.

The imaging optical system 120 related to the present embodiment is different from the conventional imaging optical system 120 shown in FIG. 10 in that the dichroic mirror 134, the half mirror 135, a dichroic mirror 136, the reflection mirror 137, the imaging lens 138, and the lens 139 and LCD 140 are provided.

The dichroic mirror 134 reflects the fundus reflection light of the illumination light from the illuminating optical system 100 (with a wavelength included within about 400 nm to 800 nm), and transmits the signal light LS (with a wavelength included within about 800 nm to 900 nm; to be described later) from the OCT unit 150. This dichroic mirror 134 is the equivalent of one example of the "optical combination and separation means" of the present invention.

Furthermore, the dichroic mirror 136 transmits the illumination light with a wavelength in the visible region from the illuminating optical system 100 (the visible light of a wavelength within about 400 nm to 700 nm for outputting from the observation optical source 101). This dichroic mirror 136 is the equivalent of one example of the "optical separation means" of the present invention.

The LCD 140 shows an internal fixation target, etc. The light from this LCD 140 is reflected by the half mirror 135 after being converged by the lens 139, and reflects the dichroic mirror 136 through the field lens 128. Further, it enters the eye to be examined E passing through the imaging lens 126, the relay lens 125, the variable magnifying lens 124, the aperture mirror 112 (aperture part 112a thereof), the objective lens 113, etc. As a result, an internal fixation target, etc. is displayed in a fundus oculi Ef of an eye to be examined E.

The image pick up element 10a is the image pick up element of CCD and CMOS, etc. installed internally in an imaging device 10 such as a TV camera, and is particularly used for detecting light of a wavelength in the near-infrared region (that is, the imaging device 10 is the infrared TV camera for detecting near-infrared light). The imaging device 10 outputs the image signal as a result of detecting near-infrared light. A touch panel monitor 11 displays a 2-dimensional image (fundus image Ef') of the surface of the fundus oculi Ef based on this image signal. Also, this image signal is sent to the arithmetic and control unit 200, and the fundus oculi image is displayed on the display (to be described later). Furthermore, when the fundus oculi are being imaged by this imaging device 10, the illumination light output from the imaging light source 103 of the illuminating optical system 100, having a wavelength in the near-infrared region, is used. This imaging device 10 (of the image pick up element 10a) is the equivalent of one example of the "first detecting means."

Also, the image pick up element 12a is the image pick up element of CCD and CMOS, etc. installed internally in an imaging device 12 such as a TV camera, and is particularly used for detecting light of a wavelength in the visible region (that is, the imaging device 12 is the TV camera for detecting visible light). The imaging device 12 outputs the image signal as a result of detecting visible light. A touch panel monitor 11 displays a 2-dimensional image (fundus image Ef') of the surface of the fundus oculi Ef based on this image signal. Also, this image signal is sent to the arithmetic and control unit 200, and the fundus oculi image is displayed on the display (to be described later). Furthermore, when the fundus oculi are being imaged by this imaging device 12, the illumination light output from the observation light source 101 of the illuminating optical system 100, having a wavelength in the visible region, is used. This imaging device 12 (of the image pick up element 12a) is the equivalent of one example of the "third detecting means."

Furthermore, the imaging optical system 120 of the present embodiment is provided with a scanning unit 141 and a lens 142. The scanning unit 141 is equipped with a constitution to scan the light output (signal light LS; to be described later) from the OCT unit 150 on a fundus oculi Ef.

The lens 142 incidents the signal light LS from the OCT unit 150 in the form of parallel light flux onto the scanning unit 141. Furthermore, the lens 142 acts so as to converge the fundus reflection light of the signal light LS that has reached through the scanning unit 141.

In FIG. 2, one example of a concrete constitution of the scanning unit 141 is shown. The scanning unit 141 is comprised including Galvanometer mirrors 141A, 141B, and reflection mirrors 141C, 141D.

The Galvanometer mirrors 141A and 141B are to be rotatable centering around rotary shafts 141a and 141b respectively. The rotary shaft 141a and 141b are arranged perpendicular to each other. In FIG. 2, the rotary shaft 141a of the Galvanometer mirror 141A is arranged parallel to the paper face on the same figure, while the rotary shaft 141b of the Galvanometer mirror 141B is arranged perpendicular to the paper face in the same figure. That is, the Galvanometer mirror 141B is to be rotatable in the directions indicated by an arrow pointing in both directions in FIG. 2, while the Galvanometer mirror 141A is to be rotatable in the directions perpendicular to the arrow pointing in both directions. As a result, this pair of Galvanometer mirrors 141A and 141B act so that the reflecting direction of the signal light LS changes to a direction perpendicular to each other. Furthermore, the rotary movement of the Galvanometer mirror 141A and 141B respectively is driven by a drive mechanism to be described later(see FIG. 5).

The signal light LS reflected by the Galvanometer mirrors 141A and 141B is to be reflected by reflection mirrors 141C and 141D, and is to advance in the same direction as having entered into the Galvanometer mirror 141A.

As described previously, a conductive optical fiber 152a runs inside the connection line 152, and the end face 152b of the optical fiber 152a is arranged opposing the lens 142. The signal light LS emitted from this end face 152b advances while gradually expanding its beam diameter toward the lens 142 until being converged to a parallel light flux by this lens 142. On the contrary, the fundus reflection light of the signal light LS is converged toward the end face 152b by this lens 142.

Constitution of OCT Unit

Next, referring to FIG. 3, the constitution of an OCT unit 150 is described. The OCT unit 150 shown in the same figure has substantially the same optical system as a conventional optical image measuring device, and is equipped with an interferometer that splits the light output from a light source into reference light and signal light, and generates interference light by the reference light that has passed through a reference object and by the signal light that has passed through an object to be measured (fundus oculi Ef), and at the same time, is configured to form images of the object to be measured by analyzing the detection result of this interference light.

A low coherence light source 160 is composed of a broad band light source such as super luminescent diode (SLD) that outputs low coherence light LO or a light emitting diode (LED), etc. This low coherence light LO, for instance, has a wave length in the near-infrared region and is supposed to be light having a time wise coherence length of approximately several tens of micro-meters. The low coherence light LO output from the low coherence light source 160 has a longer wavelength than the illumination light (wavelength: about 400 nm to 800 nm) of the fundus camera unit 1A, for example, a wavelength included within about 800 nm to 900 nm. This low coherence light source 160 corresponds to an example of the "light source" of the present invention.

The low coherence light LO output from the low coherence light source 160 is guided to an optical coupler 162 through an optical fiber 161 composed of, e.g. a single mode fiber, or PM (Polarization maintaining) fiber, and then split into reference light LR and signal light LS.

Furthermore, the optical coupler 162 has both actions, i.e. a means for splitting the light (splitter), and a means for overlaying the light (coupler); however, herein conventionally referred to as an "optical coupler".

The reference light LR generated by the optical coupler 162 is guided by an optical fiber 163 consisting of such as a single mode fiber, and emitted from the end face of the fiber. The emitted reference light LR is reflected by a reference mirror 174 (reference object) through a glass block 172 and a density filter 173 after having been converged into a parallel light flux by a collimator lens 171.

The reference light LR reflected by the reference mirror 174 is converged to the end face of the fiber of the optical fiber 163 by the collimator lens 171 again through the density filter 173 and the glass block 172. The converged reference light LR is guided to the optical coupler 162 through the optical fiber 163.

Furthermore, the glass block 172 and the density filter 173 act as a delaying means to match the optical path length (optical distance) between the reference light LR and the signal light LS, and as a means to match the dispersion characteristics of reference light LR and the signal light LS.

Furthermore, the reference mirror 174 is provided to be movable in the propagating direction of the reference light LR. As a result, it ensures the light path length of the reference light LR according to the length of the eyeball, etc. of an eye to be examined E,. Moreover, the reference mirror 174 is operated to move by a drive mechanism including a motor, etc.

Whereas, the signal light LS generated by the optical coupler 162 is guided to the end part of the connection line 152 by an optical fiber 164 consisting of such as a single mode fiber. A conductive optical fiber 152*a* runs inside the connection line 152. Herein, the optical fiber 164 and the optical fiber 152*a* may be composed of a single optical fiber, or may be jointly formed by connecting each end. In either case, it is sufficient as long as the optical fiber 164 and 152*a* are composed so as to be capable of transferring the signal light LS between the fundus camera unit 1A and the OCT unit 150.

The signal light LS is guided within the connection line 152 to the fundus camera unit 1A. Then, the signal light LS enters into the eye to be examined E through the lens 142, the scanning unit 141, the dichroic mirror 134 the imaging lens 126, the relay lens 125, the variable magnifying lens 124, the imaging diaphragm 121, the aperture part 112*a* of an aperture mirror 112, and the objective lens 113 (then, as described later, the barrier filter 122 and 123 as well as the quick return mirror 127 are retracted from the optical path respectively).

The signal light LS that has entered into the eye to be examined E forms an image on a fundus oculi (retina) Ef and is then reflected. Then, the signal light LS is not only reflected on the surface of the fundus oculi Ef, but is also scattered at the refractive index boundary reaching the deep area region of the fundus oculi Ef. As a result, the signal light LS passed through the fundus Ef becomes a light containing the information reflecting the surface state of the fundus oculi Ef and the information reflecting the scattered state in the rear at the refractive index boundary of the deep area tissue. The light is simply referred as "fundus reflection light (signal light LS thereof).

The fundus reflection light of the signal light LS advances reversely on the above route and converges at the end face 152*b* of the optical fiber 152*a*, then enters into the OCT unit 150 through this optical fiber 152, and returns to the optical coupler 162 through the optical fiber 164. The optical coupler 162 overlays this signal light LS and the reference light LR reflected at the reference mirror 174 to generate interference light LC. The generated interference light LC is guided into a spectrometer 180 through an optical fiber 165 consisting of such as a single mode fiber.

Herein, the "interference light generating means" in the present embodiment is comprised of an interferometer including at least an optical coupler 162, an optical fiber 163 and 164, and a reference mirror 174. Furthermore, although a Michelson type interferometer has been adopted in the present embodiment, for instance, a Mach Zender type, etc. or any optional type of interferometer may be adopted appropriately.

The spectrometer 180 is comprised of a collimator lens 181, a diffraction grating 182, an image forming lens 183, and a CCD (Charge Coupled Device) 184. The diffraction grating 182 in the present embodiment is a transmission type diffraction grating; however, needless to say, a reflection type diffraction grating may also be used. Furthermore, needless to say, in place of CCD 184, it is also possible to adopt other photo-detecting elements. This photo-detecting element is the equivalent of one example of the "second detecting means" of the present invention.

The interference light LC made incident onto the spectrometer 180 is to be split (spectral resolution) by the diffraction grating 182 after having been converged into a parallel light flux by the collimator lens. The split interference light LC forms an image on the image pick up surface of the CCD 184 by the image forming lens 183. The CCD 184 receives this interference light LC that is to be converted to an electrical detection signal, and outputs this detection signal to the arithmetic and control unit 200.

Constitution of Arithmetic and Control Unit

Next, the configuration of the the arithmetic and control unit 200 is described. This arithmetic and control unit 200 analyzes the detection signal input from the CCD 184 of the spectrometer 180 of the OCT unit 150, and performs a process of forming tomographic images of a fundus oculi Ef of an eye to be examined E. The analysis technique then is the same technique as the conventional Fourier domain OCT technique. Furthermore, the arithmetic and control unit 200 executes the control of each part of the fundus camera unit 1A and the control of each part of the OCT unit 150.

Also, the arithmetic and control unit 200 operates to form a 2-dimensional image showing the state of the surface of a fundus oculi Ef (retina) based on the image signal output from the imaging device 10 and 12 of the fundus camera unit 1A.

Furthermore, the arithmetic and control unit 200 executes the control of each part of the fundus camera unit 1A and the control of each part of the OCT unit 150.

As for the control of the fundus camera unit 1A, to be controlled is, for example: controlling the output of illumination light by the observation light source 101 or the imaging light source 103; controlling the insertion/retraction operation of the exciter filters 105, 106, or the barrier filters 122, 123 on the optical path; controlling the display operation of the liquid crystal display 109; controlling the shift of the illumination diaphragm 110 (controlling the diaphragm value); controlling the diaphragm value of the imaging diaphragm 121; controlling the shift of the variable magnifying lens 124 (controlling the magnification), etc. Furthermore, the arithmetic and control unit 200 performs a control of rotary operations of the Galvanometer mirrors 141A, 141B within the scanning unit 141.

Whereas, as for the control of the OCT unit 150, output control of the low coherence light by a low coherence light source 160, control of accumulated time of the CCD 184, and movement control of reference mirror 174, etc. are to be performed.

The hardware configuration of the arithmetic and control unit 200 that acts as described above is explained referring to FIG. 4. The arithmetic and control unit 200 is provided with a hardware configuration that is the same as conventional computers. To be specific, the configuration includes: a microprocessor 201 (CPU,MPU, etc.), a RAM202, a ROM203, a hard disk drive (HDD) 204, a key board 205, a mouse 206, a display 207, an image forming board 208, and a communication interface (I/F)209. Each part of these is connected through a bus 200*a*.

The microprocessor 201 executes operations characteristic to the present embodiment by rolling out a control program 204*a* that has been stored in the hard disk drive 204, on the RAM 202.

Furthermore, the microprocessor 201 executes control of each part of the devices that have previously been described and various arithmetic processes, etc. Moreover, control of each part of the devices that respond to an operation signal from the key board 205 or the mouse 206, control of display processes by the display 207, and control of transmitting/receiving processes of various types of data or control signals, etc. are executed by the communication interface 209.

The key board 205, the mouse 206 and the display 207 are used as a user interface of the fundus observation device 1. The key board 205 is used as a device for entering letters or figures, etc. by typing. The mouse 206 is used as a device to perform various entry operations with respect to the display screen of the display 207.

Furthermore, the display 207 as an optional display device such as LCD (Liquid Crystal Display) or CRT (Cathode Ray Tube), etc. displays images of a fundus oculi Ef formed by the fundus observation device 1 and displays various operation screens or set up screens, etc.

Furthermore, the user interface of the fundus observation device 1 is not limited to such a configuration but may be configured by using an optional user interface means equipped with a function to display and output various information such as track ball, control lever, touch panel type LCD, control panel for ophthalmology examinations, and with a function to input various information.

An image forming board 208 is a dedicated electronic circuit for operating to form the image of the fundus oculi Ef of an eye to be examined E. In this image forming board 208, the fundus image forming board 208a and OCT image forming board 208b are installed. The fundus image forming board 208a is a dedicated electronic circuit for operating in order to form the image of the fundus oculi based on the image signal from the imaging device 10 and the imaging device 12 of the fundus camera unit 1A. Furthermore, the OCT image forming board 208b is a dedicated electronic circuit for operating in order to form fundus images (tomographic images) based on the detecting signal from CCD 184 of the spectrometer 180 in the OCT unit 150. The image forming board 208 allows the processing speed for forming fundus images to improve.

A communication interface 209 operates to send the control signal from a microprocessor 201 to the fundus camera unit 1A and OCT unit 150. Also, the communication interface 209 operates to receive the image signal from the imaging device 10 and 12 in the fundus camera unit 1A and the detecting signal from CCD 184 in the OCT unit 150, and it operates to input the image forming board 208. At this time, the communication interface 209 operates to input the image signal from the imaging device 10 and 12 to the fundus image forming board 208a, and it operates to input the detecting signal from CCD 184 to OCT image forming board 208b.

Moreover, when the arithmetic and control unit 200 is connected to a network such as LAN (Local Area Network) or Internet, etc., the communication interface 209 may be configured to be equipped with a network adopter such as LAN card, etc. or a communication equipment such as modem, etc. so as to be able to perform data communication through the network. In this case, a server accommodating the control program 204a may be installed, and at the same time, the arithmetic and control unit 200 may be configured as a client terminal of the server.

Control System Configuration

The configuration of the control system of the fundus observation device 1 having the configuration described above is explained referring to FIG. 5. FIG. 5 shows a part related to the operations or processes of the present embodiment that has been particularly selected from among constituents composing the fundus observation device 1.

The control system of the fundus observation device 1 is configured mainly having a controlling part 210 of the arithmetic and control unit 200. The controlling part 210 is comprised including: the microprocessor 201, the RAM202, the ROM203, the hard disk drive 204 (control program 204a), and the communication interface 209.

The controlling part 210 executes said controlling processes by the microprocessor 201 that is operated based on the control program 204a. Particularly, by controlling the mirror drive mechanisms 241, 242 of the fundus camera unit 1A respectively, the Galvanometer mirrors 141A, 141B respectively may be operated independently.

Furthermore, the controlling part 210 executes control for displaying two kinds of images produced by the fundus observation device 1: that is, a 2-dimensional image (fundus image Ef) of the surface of a fundus oculi Ef by the fundus camera unit 1A, and an image(sectional image, 3-dimensional image, etc.) of a fundus oculi Ef formed based on the detection signal obtained by the OCT unit 150, parallel to each other on the display 207 of the user interface 240. These fundus images are simultaneously displayed on the display 207 respectively.

An image forming part 220 is intended to operate the process forming the fundus image based on the image signal from the imaging device 10 and 12 of the fundus camera unit 1A and to operate the process forming the fundus image based on the detecting signal from CCD 184 in the OCT unit 150, including the image forming board 208.

The image processing part 230 is used for various image processes to the fundus images formed by the image forming part 220. For example, it operates to form a 3-dimensional image of the fundus oculi Ef based on the tomographic images of the fundus oculi Ef corresponding to the detection signal from the OCT unit 150 and executes various corrections, such as brightness adjustment.

The user interface (UI) 240 is equipped with operational devices such as a key board 205 or a mouse 206, etc. and with a display device such as a display 207, etc.

The controlling feature of the scanning signal light LS by the controlling part 210 and the process feature to the detecting signal from the OCT unit 150 by the image forming part 220 and the image processing part 230 are respectively described below. Furthermore, an explanation regarding the process of the image forming part 220, etc., to the image signal from the fundus camera unit 1A is omitted because it is the same as the conventional process.

Regarding the Signal Light Scanning

Scanning of signal light LS is performed by changing the facing direction of the reflecting surfaces of the Galvanometer mirrors 141A and 141B of the scanning unit 141 in the fundus camera unit 1A. By controlling the mirror drive mechanisms 241 and 242 respectively, the controlling part 210 changes the facing direction of the reflecting surfaces of the Galvanometer mirror 141A and 141B, and scans the signal light LS on the fundus oculi Ef.

Once the facing direction of the reflecting surface of the Galvanometer mirror 141A is changed, the signal light LS is scanned in a horizontal direction (x-direction in FIG. 1) on the fundus oculi Ef. Whereas, once the facing direction of the reflecting surface of the Galvanometer mirror 141A is changed, the signal light LS is scanned in a vertical direction (y-direction in FIG. 1) on the fundus oculi Ef. Furthermore, by changing the facing direction of the reflecting surfaces of both Galvanometer mirrors 141A and 141B simultaneously, the signal light LS may be scanned in the combined x-direction and y-direction. That is, by controlling these two Galvanometer mirrors 141A and 141B, the signal light LS may be scanned in an arbitrary direction on the xy plane.

FIG. 6 represents one example of scanning features of signal light LS for forming images of a fundus oculi Ef. FIG. 6 (A) represents one example of scanning features of the signal light LS, when the signal light LS sees the fundus oculi Ef from an incident direction onto the eye to be examined E (that is, +direction of z is seen from −direction of z in FIG. 1). Furthermore, FIG. 6 (B) represents one example of arrangement features of scanning points (positions at which image measurement is carried out) on each scanning line on the fundus oculi Ef.

As shown in FIG. 6 (A), the signal light LS is scanned within a rectangular shaped scanning region R that has been preset. Within this scanning region R, plural (m number of) scanning lines R1 through Rm have been set in the x-direction. When the signal light LS is scanned along each scanning line Ri (i=1 through m), detection signals of interference light LC are to be generated.

Herein, the direction of each scanning line Ri is referred as the "main scanning direction" and the orthogonally crossing direction is referred as the "sub-scanning direction". Therefore, the scanning of the signal light LS in a main scanning direction is performed by changing the facing direction of the reflecting surface of the Galvanometer mirror 141A, and the scanning in a sub-scanning direction is performed by changing the facing direction of the reflecting surface of the Galvanometer mirror 141B.

On each scanning line Ri, as shown in FIG. 6 (B), plural (n number of) of scanning points Ri1 through Rin have been preset.

In order to execute the scanning shown in FIG. 6, the controlling part 210 controls the Galvanometer mirrors 141A and 141B to set the incident target of the signal light LS with respect to a fundus oculi Ef at a scan start position RS(scanning point R11) on the first scanning line R1. Subsequently, the controlling part 210 controls the low coherence light source 160 to flush the low coherence light LO for emitting the signal light LS to the scan start position RS. The CCD 184 receives the interference light LC based on the fudus reflection light of this signal light LS at the scan start position RS, and outputs detection signals to the controlling part 210.

Next, by controlling the Galvanometer mirror 141A the controlling part 210 scans the signal light LS in a main scanning direction and sets the incident target at a scanning point R12, triggering a flush emission of the low coherence light LO for making the signal light LS incident onto the scanning point R12. The CCD 184 receives the interference light LC based on the fundus reflection light of this signal light LS at the scanning point R12, and then outputs the detection signal to the controlling part 210.

Likewise, the controlling part 210 obtains detection signals output from the CCD 184 responding to the interference light LC with respect to each scanning point, by flush emitting the low coherence light LO at each scanning point while shifting the incident target of the signal light LS from scanning point R13, R14, - - - , R1 (n−1), R1n in order.

Once the measurement at the last scanning point R1n of the first scanning line R1 is finished, the controlling part 210 controls the Galvanometer mirrors 141A and 141B simultaneously and shifts the incident target of the signal light LS to the first scanning point R21 of the second scanning line R2 following a line switching scan r. Then, by conducting the previously described measurement with regard to each scanning point R2j (j=1 through n) of this second scanning line R2, a detection signal corresponding to each scanning point R2j is obtained.

Likewise, by conducting a measurement with respect to the third scanning line R3, - - -, the m−1th scanning line R (m−1), the mth scanning line Rm respectively to obtain the detection signals corresponding to each scanning point. Furthermore, the symbol RE on a scanning line Rm is a scan end position in accordance with a scanning point Rmn.

As a result, the controlling part 210 obtains m×n number of detection signals corresponding to m×n number of scanning points Rij (i=1 through m, j=1 through n) within the scanning region R. Hereinafter, a detection signal corresponding to the scanning point Rij may be represented as Dij.

Such interlocking control of such shifting of scanning points and the output of the low coherence light LO may be realized by synchronizing, for instance, the transmitting timing of control signals with respect to the mirror drive mechanisms 241, 242 and the transmitting timing of control signals (output request signal) with respect to the low coherence light source 160.

As described, when each Galvanometer mirror 141A and 141 B is being operated, the controlling part 210 stores the position of each scanning line Ri or the position of each scanning point Rij (coordinate on the xy coordinate system) as information indicating the content of the operation. This stored content (scan positional information) is used in an image forming process as was conducted conventionally.

Regarding Image Processing

Next, one example of the process relating to OCT images is described of the image forming part 220 and the image processing part 230.

The image forming part 220 executes the formation process of tomographic images of a fundus oculi Ef along each scanning line Ri (main scanning direction). The image processing part 230 executes the formation process of a 3-dimensional image of the fundus oculi Ef based on these tomographic images formed by the image forming part 220.

The formation process of a tomographic image by the image forming part 220, as was conventionally done, includes a 2-step arithmetic process. In the first step of the arithmetic process, based on a detection signal Dij corresponding to each scanning point Rij, an image in the depth-wise direction (z-direction in FIG. 1) of a fundus oculi Ef at the scanning point Rij is formed.

FIG. 7 represents a feature of a tomographic image formed by the image forming part 220. In the second step of the arithmetic process, with regard to each scanning line Ri, based on the images in the depth-wise direction at the n number of scanning points Ri1 through Rin thereon, a tomographic image Gi of a fundus oculi Ef along this scanning line Ri is formed. Then, the image forming part 220 determines the arrangement and the distance of each scanning point Ri1 through Rin while referring to the positional information (said scan positional information) of each scanning point Ri1 through Rin, and forms this scanning line Ri. Due to the above process, m number of tomographic images G1 through Gm at different positions of the sub-scanning direction (y-direction) are obtained.

Next, the formation process of a 3-dimensional image of a fundus oculi Ef by the image processing part 230 is explained. A 3-dimensional image of a fundus oculi Ef is formed based on the m number of tomographic images obtained by the above arithmetic process. The image processing part 230 forms a 3-dimensional image of the fundus oculi Ef by performing a publicly known interpolating process to interpolate an image between the adjacent tomographic images Gi and G (i+1).

Then, the image processing part 230 determines the arrangement and the distance of each scanning line Ri while referring to the positional information of each scanning line Ri to form this 3-dimensional image. For this 3-dimensional image, a 3-dimensional coordinate system (x,y,z) is set up, based on the positional information (said scan positional information) of each scanning point Rij and the z coordinate in the images of the depth-wise direction.

Furthermore, based on this 3-dimensional image, the image processing part 230 is capable of forming a tomographic image of the fundus oculi Ef at a cross-section in an arbitrary direction other than the main scanning direction (x-direction). Once the cross-section is designated, the image processing part 230 determines the position of each scanning point (and/or an image in the depth-wise direction that has been interpolated) on this designated cross-section, and extracts an image (and/or image in the depth-wise direction that has been interpolated) in the depth-wise direction at each determined position to form a tomographic image of the fundus oculi Ef at the designated cross-section by arranging plural extracted images in the depth-wise direction.

Furthermore, the image Gmj in FIG. 7 represents an image in the depth-wise direction (z-direction) at the scanning point Rmj on the scanning line Rm. Likewise, an image in the depth-wise direction at each scanning point Rij on the scanning line Ri formed by the arithmetic process of said first step may be represented as "image Gij."

Operation and Effect

The operation and effect of the fundus observation device 1 related to the present embodiment having the constitution as above is explained.

This fundus observation device 1 comprises the fundus camera unit 1A for operating as the fundus camera in order to capture 2-dimensional images showing the state of the surface of the fundus oculi Ef and the OCT unit 150 for operating as an optical image measuring device in order to capture tomographic images (and 3-dimensional images) of the fundus oculi Ef.

The optical path of the signal light used for image forming by the OCT unit 150 is guided to an eye to be examined E by combining the optical path (the optical path for imaging) for forming by the imaging optical system 120 of the fundus camera unit 1A. The combining of this optical path is performed by the dichroic mirror 134.

In addition, the fundus reflection light of the signal light LS is guided to the dichroic mirror 134 along the optical path for imaging, and goes to the OCT unit 150 by being separated from the optical path for imaging via this dichroic mirror 134.

As a result, by setting the dichroic mirror 134 for operating in order to combine and separate the optical path for imaging of the fundus camera unit 1A and the optical path of the signal light LS, it is possible to capture both 2-dimensional images of the surface of the fundus oculi Ef and tomographic images of the fundus oculi Ef (and 3-dimensional images).

In particular, to an eye to be examined E, if illumination of the illumination light by the fundus camera unit 1A and illumination of the signal light LS by the OCT unit 150 are simultaneously operated, each fundus reflection light can be separated via the dichroic mirror 134 and images formed by detecting each of them, making it possible to simultaneously produce both 2-dimensional images of the surface of the fundus oculi Ef and tomographic images of the fundus oculi Ef.

At this time, the signal light LS from the OCT unit 150 and the simultaneously illuminated light may be near-infrared light from the imaging light source 103 and also visible light from the observation light source 101.

MODIFIED EXAMPLE

The constitution described above is merely one example to preferably implement the fundus observation device related to the present invention. Therefore, optional modifications may be implemented appropriately within the scope of the present invention.

For example, in the above embodiment, as the low coherence light LO, near-infrared light with a wavelength of about 800 nm to 900 nm is used, but light of longer wavelengths can be used to measure images in the deeper region of the fundus oculi Ef. For example, near-infrared light of a wavelength within about 900 nm to 1000 nm is used, and also near-infrared light of a wavelength within about 1000 nm to 1100 nm can be used.

Moreover, when low coherence light LO of a wavelength within about 900 nm to 1000 nm is used, the near-infrared light of a wavelength within about 700 nm to 900 nm can be used as the illumination light for the fundus camera unit 1A. Moreover, when the low coherence light LO of a wavelength within about 1000 nm to 1100 nm is used, near-infrared light of a wavelength within about 850 nm to 1000 nm can be used as the illumination light for the fundus camera unit 1A. Herein, in each case, it is desirable to set a longer wavelength for the low coherence light LO than the wavelength of the illumination light of the fundus camera unit 1A, but it is possible to adapt the constitution such that the relationship of short and long wavelengths is reversed.

A first image forming means of the fundus observation device related to the present embodiment is not limited to a fundus camera (unit), an arbitrary ophthalmologic device capable of forming a 2-dimensional image of a fundus surface may also be applied. For example, a slit lamp (slit lamp microscopic device) may be used as a first image forming means.

Moreover, in the above embodiment, the forming process of the fundus image by the image forming part 220 (image forming board 208) and each controlling process are operated by the control part 210 (microprocessor 201, etc.), but it can be composed to operate these two processes by one or several computers.

Embodiment 2

The fundus observation device related to Embodiment 2 is described. The fundus observation device of the embodiment has the same constitution of the fundus observation device 1 of the first embodiment (see FIG. 1 to FIG. 4). Moreover, the scanning features of signal light by the fundus observation device of the embodiment and the forming features of tomographic images are the same as FIG. 6 and FIG. 7. The fundus observation device of the present embodiment is described below with regard to the differences from Embodiment 1.

FIG. 8 shows one example of the constitution of a control system of the fundus observation device of this embodiment. The fundus observation device 20 shown in the same figure is provided with a fundus camera unit 1A, an OCT unit 150 and an arithmetic and control unit 200.

Herein, the constitution of the optical path of the reference light LR is described. First, an optical fiber 163 guiding the reference light LR has a constitution such that it allows the effect of dispersion, which is nearly equal to the effect of the dispersion assignment at the time when the signal light LS generated by the optical coupler 162 is overlapped with the reference light LR through the fundus oculi Ef, to the reference light LR.

That is, the reference light LR is allowed and guided as an aberration of the effect of dispersion by the core of this optical fiber 163. Moreover, the signal light LS enters the eye to be examined E through the optical fiber 164, the optical fiber 152a inside the connection line 152, the lens 142, the scanning unit 141, the dichroic mirror 134, the imaging lens 126, the relay lens 125, the variable magnifying lens 124, the imaging diaphragm 121, the aperture part 112a of an aperture mirror 112, and the objective lens 113, and the signal light LS emitted from an eye to be examined E returns to the optical coupler 162 by going back along this path. At this time, when the signal light LS passes through each optical element of the optical fiber 164, 152a, the lens 142, the dichroic mirror 134, the imaging lens 126, the relay lens 125, the variable magnifying lens 124, and the object lens 113, the aberration is allowed by the effect of dispersion by the optical element. The effect of dispersion by these optical elements (the amount of dispersion) can be calculated based on the characteristic (refractive index, etc.) of the materials forming the optical element. In addition, the device for measuring the dispersion allowed by the light is also widely used.

The optical fiber 163 guiding the reference light LR is formed to have a fiber length that allows dispersion, which is nearly equal to the total value of the dispersion allowing these optical elements to the signal light LS, to the reference light LR. At this time, the optical fiber 163 has a fiber length capable of reducing the dispersion allowed by said glass block 172 and a density filter 173. That is, the optical fiber 163, glass block 172, and the density filter 173 are composed such that they allow dispersion which is nearly equal to the dispersion allowing the above optical element to the signal light LS.

Moreover, the signal light LS also affects dispersion by air on the optical path (the signal optical path), but the optical path of the reference light LR is composed to allow dispersion which is nearly equal to the dispersion to the signal light LS by this air to the reference light LR. Moreover, the effect of dispersion by this air is very small compared to the effect of dispersion by the optical element. Therefore, as the fundus observation device related to the present invention, it may be composed in consideration of the effect of dispersion by the optical element only. In the present embodiment, taking into consideration the effect of the dispersion by this air, the accuracy of the image measuring is improved further. In addition, the glass block 172 and the density filter 173 on the reference optical path are used for allowing dispersion which is nearly equal to the dispersion allowing the signal optical path to the signal light LS, but overlap occurs over the optical length between the signal optical path and the reference optical path due to the existence of this glass block 172, etc. The overlap of this optical path can be resolved by matching the optical length of the reference optical path and the optical length of the signal optical path. For example, by designing the reference optical path to be nearly equal to the distance by which the signal light LS passes through air with the distance by which the reference light LR passes through air (for example, the disposal interval of the glass block 172, etc. is designed be of a timely interval), the overlap of the optical path length can be resolved.

On the hard disk drive 204 (see FIG. 4) of the arithmetic and control unit 200, the controlling program 204a, and all information such as the information of the patients are stored. As information on patients, the laboratory information such as patient ID (identification information) and the name of patients, and also the spherical diopter power of the eyeball optical system of an eye to be examined, the degree of astigmatism, the axis degree of astigmatism, the radius of curvature of the cornea, and the astigmatism, is included.

The arithmetic and control unit 200 of this embodiment has a correcting processing part 250. The correcting processing part 250 performs processing to correct OCT image of the fundus oculi Ef (tomographic image and 3-dimensional image) based on the aberration of eyeball optical system of an eye to be examined E stored on the hard disk drive 204 of the controlling part 210. For example, the controlling processing part 250 corrects the effect of the aberration of the eyeball optical system of an eye to be examined regarding each tomographic image Gi. Herein, the aberration of the eyeball optical system of an eye to be examined can be measured by the eye characteristic measuring device disclosed in Japanese Patent laid-open Application No. 2002-306416 by this applicant, etc. Moreover, this eye characteristic measuring device can also measure higher-order aberrations of the eyeball optical system. Aberration correction of OCT images by the correction processing part 250 can be performed accordingly with any method in existence. This correcting processing part 250 acts as an example of the "correcting means" of the present embodiment.

The operation and effect of the fundus observation device 20 related to the present embodiment is explained.

This fundus observation device 20 comprises the fundus camera unit 1A for operating as the fundus camera in order to capture 2-dimensional images showing the state of the surface of the fundus oculi Ef and the OCT unit 150 for operating as an optical image measuring device in order to capture tomographic images (and 3-dimensional images) of the fundus oculi Ef.

The optical path of the signal light used for image forming by the OCT unit 150 is guided to an eye to be examined E by combining the optical path (the optical path for imaging) for forming by the imaging optical system 120 of the fundus camera unit 1A. The combining of this optical path is performed by the dichroic mirror 134.

In addition, the fundus reflection light of the signal light LS is guided to the dichroic mirror 134 along the optical path for imaging, and goes to the OCT unit 150 by being separated from the optical path for imaging via this dichroic mirror 134.

As a result, by setting the dichroic mirror 134 for operating in order to combine and separate the optical path for imaging of the fundus camera unit 1A and the optical path of the signal light LS, it is possible to capture both 2-dimensional images of the surface of the fundus oculi Ef and tomographic images of the fundus oculi Ef (and 3-dimensional images).

In particular, to an eye to be examined E, if illumination of the illumination light by the fundus camera unit 1A and illumination of the signal light LS by the OCT unit 150 are simultaneously operated, each fundus reflection light can be separated via the dichroic mirror 134 and images formed by detecting each of them, making it possible to simultaneously produce both 2-dimensional images of the surface of the fundus oculi Ef and tomographic images of the fundus oculi Ef.

At this time, the signal light LS from the OCT unit 150 and the simultaneously illuminated light may be near-infrared light from the imaging light source 103 and also visible light from the observation light source 101.

Moreover, the fundus observation device 20 related to this embodiment has an optical fiber 163 with a fiber length that allows dispersion, which is nearly equal to the dispersion assignment at the time when the signal light LS generated by the optical coupler 162 is overlapped with the reference light LR through the fundus oculi Ef, to the reference light LR. Further, the glass block 172 allowing dispersion to the reference light LR and the density filter 173 are also comprised. In addition, by the optical fiber 163 for allowing dispersion to the reference light LR and the glass block 172, etc., overlap occurs along the optical length between the signal optical path and the reference optical path, in order to be nearly equal to the distance which the reference light LR passes through air with the distance which the signal light LS passes through air, and the overlap of this optical path length can be resolved by setting the reference optical path.

That is, this fundus observation device 20 is composed to be nearly equal to the total value of the dispersion of several optical elements through the signal light LS and the total value of the dispersion of several optical element through the reference light LR, and is also composed to be nearly equal to the optical length of the signal light path and the optical length of the reference light.

According to such fundus observation device 20, the effect of dispersion to the signal light LS and the effect of dispersion to the reference light LR are nearly equal, so it can interfere the signal light LS and the reference light LR with high interference efficiency, and it can generate sufficient intensity interference light LC. As a result, it can prevent situations such as a decrease in the contrast of OCT images, unclear images, and a decrease in the accuracy of the image.

Furthermore, the optical fiber 163, the glass block 172, the density filter 173, and the reference optical path, which are composed as described above, correspond to an example of "dispersion assignment means" of the present embodiment, respectively.

Moreover, according to the fundus observation device 20 related to the present embodiment, based on the aberration of the eyeball optical system of an eye to be examined E, it is composed to correct OCT images (tomographic image and 3-dimensional image) of the fundus oculi Ef, so it can be improved to provide clearer and more accurate OCT images.

Next, the modification example of the fundus observation device 20 of the present embodiment is explained.

In the embodiment above, the optical fiber 163 guiding the reference light LR and the glass block 172, the density filter 173, and the reference optical path are used as "dispersion assignment means" of the present embodiment, but it is sufficient if at least one of these are used. Moreover, more than with these, as explained below, it is possible to adapt the dispersion assignment means of any form allowing the effect of dispersion to the reference light LR.

The glass block 172 maybe composed of any optical members which act so as to provide the dispersion value to the light, such as a prism. Also, alternative to the glass block 172, the dispersion assignment means comprising any materials such as resin, for example, acryl, may be provided.

Furthermore, the dispersion assignment means may be composed so as to be able to adjust the dispersion value properly to be provided to the light. For example, it may be composed by a variable prism. Also, the optical member may be used which is able to adjust the dispersion value provided to the light by fulfilling a proper amount of liquid such as water in the package.

Furthermore, since the signal light LS passes the fundus oculi Ef transmitting inside the eyeball of the eye to be examined E, "the dispersion value provided to the signal light LS" including the dispersion value which the eyeball optics of the eye to be examined provides, as well as the optical elements inside the fundus observation apparatus 20 passed by the signal light LS, should be taken into consideration, improving the precision of correction of the dispersion value. Note that the dispersion value provided by the eyeball optics can be determined by the optical property value such as the refractive index and/or the length of the eye axis of the eye to be examined E.

Meanwhile, the refractive index and/or the axis length of the eye to be examined E may be obtained by measuring in advance using other ophthalmologic device and they may be obtained by installing the function for measuring these optical property value in the fundus observation apparatus 20. Furthermore, the statistical value of the refractive index and/or the axis length may be determined using clinical data and the dispersion value provided by the eyeball optics can be obtained using the statistical value. Also, the statistical value of the dispersion value provided by the eyeball optics may be determined using clinical data and used for the correction process.

Furthermore, when the influence of the dispersion value provided by the eyeball optics is taken into consideration according to each eye to be examined, the dispersion value provided by the dispersion assignment means to the reference light LR may be constructed so as to be changeable depending on the dispersion value due to the eyeball optics. For this purpose, the dispersion assignment means able to adjust the dispersion value such as the above variable prism may be provided, the dispersion assignment means controlled by the control part 210, so that the proper dispersion value is provided to the reference light LR.

By allowing dispersion to the reference light LR with such dispersion assignment means, it can reimburse at least one part of the dispersion assignment to the signal light by the optical element and air on the optical path for imaging, and it is possible to control the decrease in the interference efficiency of the signal light LS and the reference light LR. As a result, it can decrease both the contrast of OCT images and that of accuracy.

Furthermore, the modification example explained in Embodiment 1 may be applied to the fundus observation device 20 of the present embodiment.

What is claimed is:

1. A fundus observation device comprising: a first image forming means having an illuminating optical system for emitting illumination light onto a fundus oculi of an eye to be examined and an imaging optical system for detecting the illumination light passing through said fundus oculi by a first detecting means, and forming a 2-dimensional image of the surface of said fundus oculi based on the detection results by said first detecting means;

a second image forming means having a light source which outputs light of a wavelength which is different from said illumination light, an interference optical generating means splitting said light output from said light source into the signal light directed towards said fundus oculi and the reference light directed towards a reference object and generating interference light by overlapping the signal light passing through said fundus oculi and the reference light passing through said reference object, and a second detecting means for detecting said interference light generated, and forming tomographic images of said fundus oculi based on the detected results by said second detecting means;

a common objective lens for imaging by both the first image forming means and the second image forming means to provide targeting at the same point of said fundus oculi for simultaneous imaging by said first image forming means and said second image forming means; and a separation means for separating the signal light from the first image forming means and the illumination light directed to the second image forming means, wherein said illumination optical system comprises a ring transparent plate disposed on a conjugating location with a pupil of the eye to be examined in order to illuminate the illumination light to the fundus oculi of the eye to be examined through the ring transparent plate, and said illuminating optical system and said imaging optical system comprise an aperture mirror having an aperture in a center region which guides the illumination light from the illuminating optical system to the common objective lens by reflection and which passes the illumination light from the fundus oculi through the aperture.

2. A fundus observation device according to claim 1, wherein said illumination light of said first image forming means and the signal light output by said light source of said second image forming means are light having a wavelength in the near-infrared region, respectively.

3. A fundus observation device according to claim 2, wherein said separation means separates said illumination light from said signal light having the wavelength longer than that of said illumination light.

4. A fundus observation device according to claim 3, wherein said separation means separates said illumination light having a wavelength between 700 nm to 800 nm, and the signal light having a wavelength between 800 nm to 900 nm.

5. A fundus observation device according to claim 3, wherein said separation means separates said illumination light having a wavelength between 850 nm to 1000 nm, and the signal light having a wavelength between 1000 nm to 1100 nm.

6. A fundus observation device according to claims 1, wherein said separating means is a dichroic mirror, which separates, among the combined light via said fundus oculi, said illumination light and said signal light of different wavelength from said illumination light, by reflecting said illumination light while transmitting said signal light.

7. A fundus observation device according to claims 2, wherein said illuminating optical system of said first image forming means further comprises a visible light source for outputting illumination light with a wavelength within the visible region, wherein said imaging optical system further comprises a third detecting means for detecting the illumination light with a wavelength within said visible region passing through said fundus oculi, and wherein said first image forming means forms a 2-dimensional surface image of said fundus oculi based on the detected results by said third detected means.

8. A fundus observation device according to claim 7, wherein said imaging optical system further comprises an optical path separating means for splitting the optical path of illuminating light with a wavelength in said infrared region and the optical path of illuminating light with a wavelength in said visible region.

9. A fundus observation device according to claim 1, wherein said interference optical generating means further comprises a dispersion assignment means for assigning dispersion to said reference light.

10. A fundus observation device according to claim 9, wherein said dispersion assignment means assigns to said reference light a dispersion amount generally equal to the dispersion amount assigned to said signal light during the time from said splitting to said overlapping by said interference light generating means.

11. A fundus observation device according to claim 9, wherein said dispersion assignment means includes an optical fiber which guides said reference light and said optical fiber having fiber length in order to assign a dispersion amount generally equal to the dispersion amount assigned to said signal light to said reference light.

12. A fundus observation device according to claims 9, wherein said dispersion assignment means includes a glass block that assigns a given dispersion amount to said reference light.

13. A fundus observation device according to claims 9 wherein said dispersion assignment means includes a density filter that assigns a given dispersion amount to said reference light.

14. A fundus observation device according to claims 9, further comprising a correction means for correcting a tomographic image of said fundus oculi which was formed by said second image forming means based on the aberration of the eyeball optical system of said eye to be examined.

15. A fundus observation device according to claim 1, wherein the total value of the dispersion amount of plural optical elements through which said signal light passes during the time from said splitting to said overlapping by said interference light generating means, is generally equal to the total value of the dispersion amount of plural optical elements through which said reference light passes during the time from said splitting to said overlapping by said interference light generating means.

16. A fundus observation device according to claim 15, wherein the dispersion amount that said signal light is assigned by air during the time from said splitting to said overlapping by said interference light generating means is generally equal to the dispersion amount that said reference light is assigned by air during the time from said splitting to said overlapping by said interference light generating means.

* * * * *